United States Patent
Nakanishi et al.

(10) Patent No.: US 9,678,184 B2
(45) Date of Patent: Jun. 13, 2017

(54) METHOD FOR INCREMENT OF RF-PHASE BASED ON STATIC MAGNETIC FIELD INHOMOGENEITY IN MRI APPARATUS

(71) Applicant: HITACHI, LTD., Tokyo (JP)

(72) Inventors: Kenji Nakanishi, Tokyo (JP); Hiroyuki Itagaki, Tokyo (JP); Takashi Nishihara, Tokyo (JP)

(73) Assignee: HITACHI, LTD., Tokyo (JP)

(*) Notice: Subject to any disclaimer, the term of this patent is extended or adjusted under 35 U.S.C. 154(b) by 489 days.

(21) Appl. No.: 14/365,278

(22) PCT Filed: Dec. 12, 2012

(86) PCT No.: PCT/JP2012/082139
§ 371 (c)(1),
(2) Date: Jun. 13, 2014

(87) PCT Pub. No.: WO2013/105384
PCT Pub. Date: Jul. 18, 2013

(65) Prior Publication Data
US 2014/0327440 A1 Nov. 6, 2014

(30) Foreign Application Priority Data

Jan. 11, 2012 (JP) .................................. 2012-002644
May 25, 2012 (JP) .................................. 2012-119153

(51) Int. Cl.
*G01V 3/00* (2006.01)
*G01R 33/3875* (2006.01)
(Continued)

(52) U.S. Cl.
CPC .......... *G01R 33/3875* (2013.01); *A61B 5/055* (2013.01); *G01R 33/56563* (2013.01)

(58) Field of Classification Search
CPC .......... G01R 33/3875; G01R 33/56563; A61B 5/055
(Continued)

(56) References Cited

U.S. PATENT DOCUMENTS 6,720,767 B2 4/2004 Yamazaki
8,643,364 B2 * 2/2014 Umeda .............. G01R 33/3678
324/307

(Continued)

FOREIGN PATENT DOCUMENTS

JP 2003-210431 7/2003
JP 2005-152175 6/2005
(Continued)

OTHER PUBLICATIONS

International Search Report in PCT/JP2012/082139, Feb. 5, 2013.
(Continued)

*Primary Examiner* — Susan Lee
(74) *Attorney, Agent, or Firm* — Cooper & Dunham LLP

(57) ABSTRACT

In order to reduce image quality deterioration due to static magnetic field inhomogeneity according to imaging conditions without increasing an operator workload, shimming current where static magnetic field inhomogeneity of a selected region is reduced is calculated, shimming is performed for the selected region using the calculated local Bo shimming current, and then an increment (RF-Phase) in an irradiation phase of an RF pulse that excites the selected region in a state where static magnetic field inhomogeneity of the selected region is reduced or a post-adjustment excitation frequency (f0') that is an excitation frequency is calculated. These increments (RF-Phase) in an irradiation phase and post-adjustment excitation frequency (f0') that is an excitation frequency correspond with each other in amount.

15 Claims, 13 Drawing Sheets

(51) Int. Cl.
*A61B 5/055* (2006.01)
*G01R 33/565* (2006.01)

(58) Field of Classification Search
USPC .......................................................... 324/309
See application file for complete search history.

(56) References Cited

U.S. PATENT DOCUMENTS

| | | | |
|---|---|---|---|
| 9,377,517 B2 * | 6/2016 | Witschey | G01R 33/3875 |
| 2003/0137298 A1 | 7/2003 | Yamazaki | |

FOREIGN PATENT DOCUMENTS

| | | |
|---|---|---|
| JP | 2009-50605 | 3/2009 |
| JP | 2011-229632 | 11/2011 |

OTHER PUBLICATIONS

N. K. Bangerter, "SNR Analysis of Multiple Acquisition SSFP", Proceedings of International Society for Magnetic Resonance in Medicine [CD-Rom], May 18, 2002, #475.

* cited by examiner

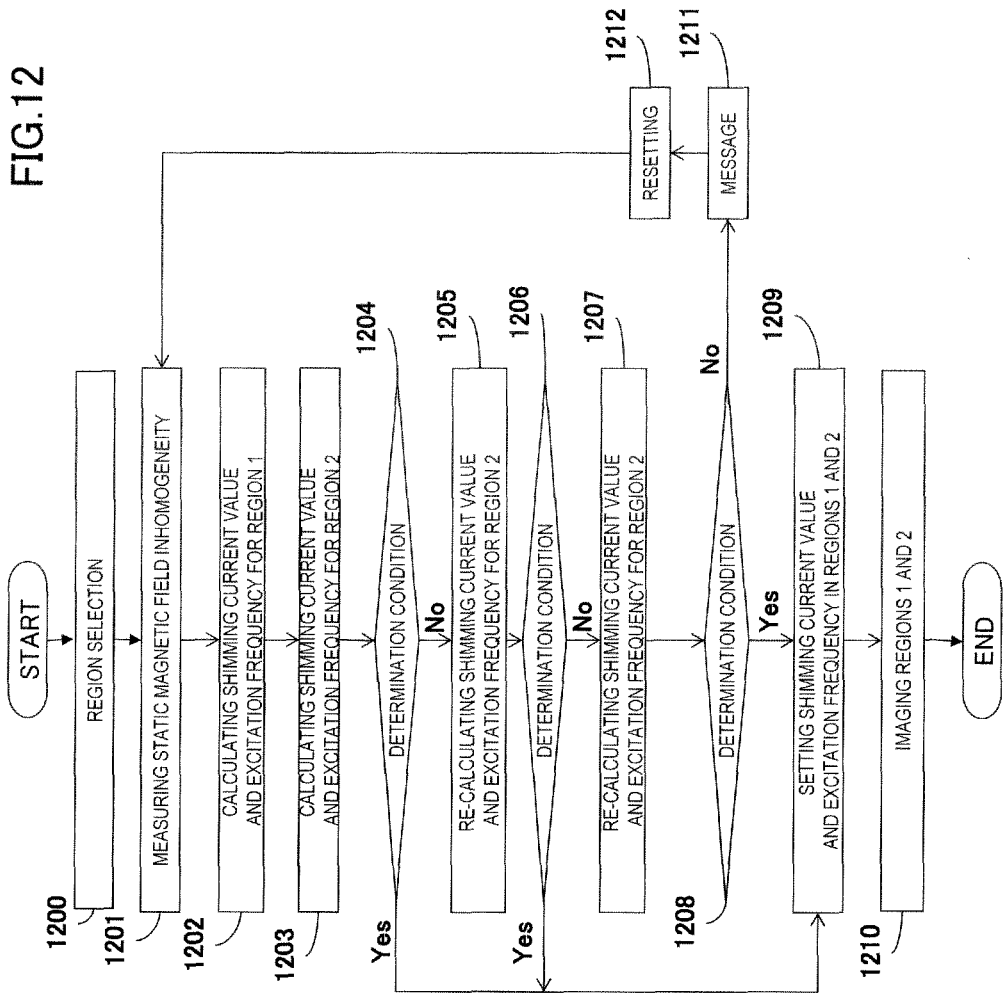

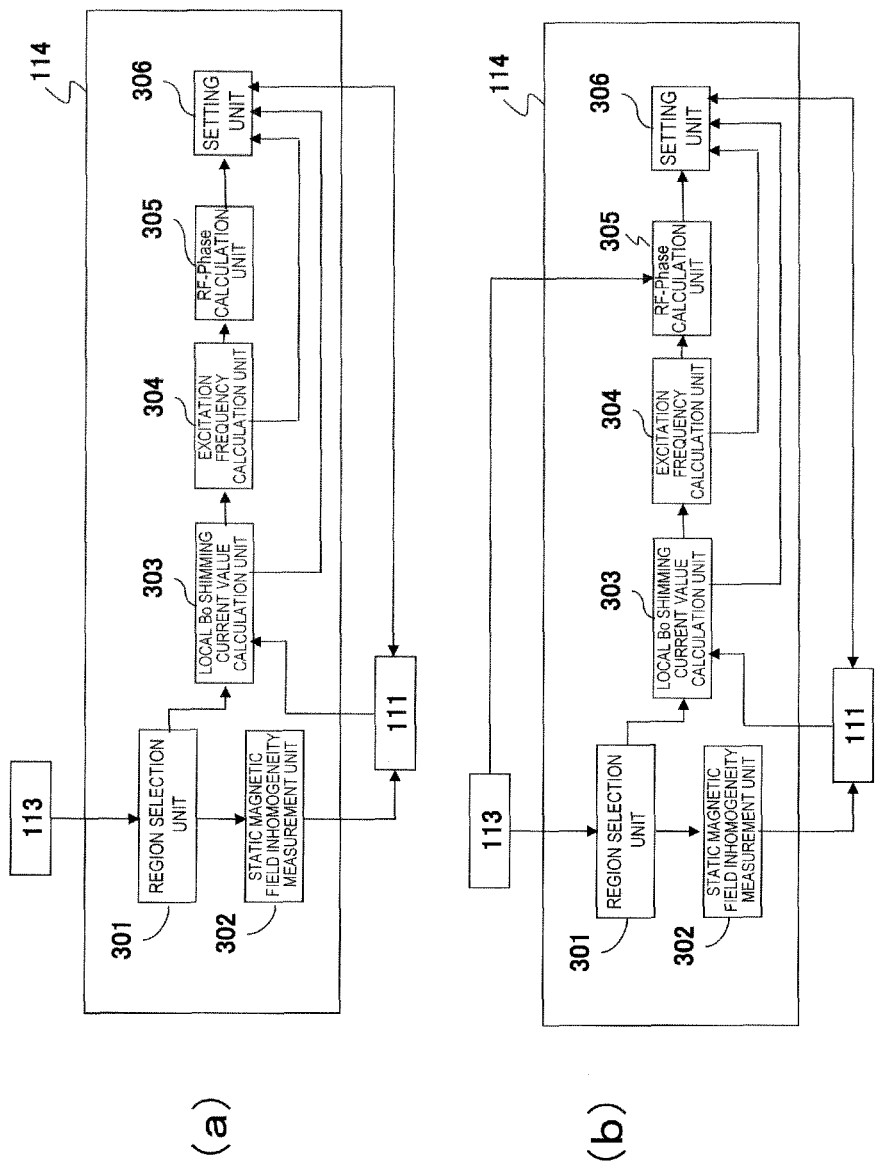

METHOD FOR INCREMENT OF RF-PHASE BASED ON STATIC MAGNETIC FIELD INHOMOGENEITY IN MRI APPARATUS

TECHNICAL FIELD

The present invention relates to a Magnetic Resonance Imaging apparatus (hereinafter, referred to as "MRI apparatus"), and in particular, to a technique for imaging a selected region according to static magnetic field inhomogeneity.

BACKGROUND ART

A MRI apparatus measures an NMR signal generated by a nuclear spin that comprises tissues of an object, particularly a human body to image forms and functions of the head, belly, limbs, etc. two-dimensionally or three-dimensionally. In imaging, a phase encode that varies depending on the gradient magnetic field as well as frequency-encoding are provided to an NMR signal, the NMR signal is measured as time-series data. The measured NMR signal is reconstructed into an image by performing a two-dimensional or three-dimensional Fourier transform.

In an ultra-high magnetic field MRI apparatus of 3 T or more, static magnetic field inhomogeneity that is spatially inhomogeneous in a static magnetic field increases. On the other hand, an SSFP (steady-state free precession) sequence that repeats measuring an echo signal in a short time with magnetization in a steady-state free precession state and an EPI (Echo Planar Imaging) sequence that measures a plurality of echo signals using a single or multiple excitations by oscillating a readout gradient magnetic field are sensitive to static magnetic field inhomogeneity. Therefore, in an image obtained using these pulse sequences in an ultra-high magnetic field MRI apparatus of 3 T or more, artifacts generated based on static magnetic field inhomogeneity are conspicuous. Also, a pencil-beam-shaped excitation using a two-dimensional excitation may deteriorate an excitation profile due to static magnetic field inhomogeneity.

Taking an SSFP sequence as an example, influence of static magnetic field inhomogeneity will be described. In the SSFP sequence, assuming RF pulse repetition time as TR, band artifacts occur in an image at a frequency where static magnetic field inhomogeneity is an odd multiple of ½ TR. When the SSFP sequence is used for cineradiography of a heart, in a 1.5 T apparatus, band artifacts occur at a position where there are no diagnostic problems in an image. However, because static magnetic field inhomogeneity increases in a 3 T apparatus, band artifacts may overlap with a cardiac short axis where band artifacts are regions of interest. Consequently, evaluation of cardiac functions such as ejection fraction may be influenced.

As a standard method to reduce static magnetic field inhomogeneity, Bo shimming that applies appropriate current to a shim coil to adjust static magnetic field homogeneity in an imaging target region is used. In particular, if static magnetic field homogeneity is increased locally, the method called local Bo shimming that generates a compensation magnetic field to reduce local static magnetic field inhomogeneity is used. Specifically, by measuring static magnetic field inhomogeneity unique to the apparatus in a case where nothing exists in an imaging space when an MRI apparatus is installed and then measuring static magnetic field inhomogeneity in an imaging space including an imaging target when imaging is performed, a compensation magnetic field that reduces static magnetic field inhomogeneity in an imaging target region using both the data is generated in a shim coil.

However, band artifacts of an SSPF sequence cannot be solved only by local Bo shimming. Therefore, in the SSPF sequence, in addition to local Bo shimming, a method that slightly shifts an excitation frequency of an RF pulse so that band artifacts do not overlap with a heart region is used. As a method to calculate the excitation frequency, a method that creates a static magnetic field inhomogeneity estimate map from static magnetic field inhomogeneity after local Bo shimming and calculates an excitation frequency to reduce average static magnetic field inhomogeneity in the cardiac short axis direction is used. Alternatively, as a preliminary measurement, the method (PTL 1) is used where imaging is performed to create a plurality of images with the excitation frequency slightly shifted, and an operator visually searches for an appropriate excitation frequency so that artifacts do not overlap on the short axis of the heart.

CITATION LIST

Patent Literature

PTL 1: Publication of U.S. Patent Application No. 2005/0165295

Non-Patent Literature

NPTL 1: M. Schar, et. al., MRM 51, p 799 (2004)

SUMMARY OF INVENTION

Technical Problem

As described above, in a case where a certain single-region like a heart is an imaging target, local Bo shimming and excitation frequency adjustment can reduce artifacts. However, even in a case where plural regions are excited separately using a pre-pulse, sensitive to static magnetic field inhomogeneity, such as a pencil beam, when the plural regions are imaged using the same local Bo shimming and excitation frequency, image quality deterioration caused by static magnetic field inhomogeneity occurred in any of the regions.

Also, if an operator accidentally changes an excitation frequency from a spectrum shape after measuring a cross-section spectrum of imaging slices when using an SSFP sequence, the position of band artifacts is unintentionally shifted from an appropriate position. Also, even after the above local Bo shimming and excitation frequency are adjusted, if the position of the band artifacts is not appropriate, this will be a difficult adjustment for the operator.

Therefore, the present invention was made in light of the above problems, and the aim is to provide an MRI apparatus and a region imaging method that can reduce image quality deterioration due to static magnetic field inhomogeneity according to an imaging condition without increasing an operator's burden.

Solution to Problem

To solve the above problems, the present invention calculates shimming current in which static magnetic field inhomogeneity in a selected region is reduced, performs shimming for the selected region using the calculated local Bo shimming current, and then calculates an increment during the irradiation phase of an RF pulse that excites the selected region (RF-Phase) in a state where static magnetic field inhomogeneity in the selected region is reduced or a post-adjustment excitation frequency that is an excitation frequency (f0'). The increment during the irradiation phase (RF-Phase) and the post-adjustment excitation frequency that is an excitation frequency (f0') correspond with each other in amount. Then, an RF pulse using at least either of the increments during the irradiation phase (RF-Phase) or the post-adjustment excitation frequency that is an excitation frequency (f0') is used for imaging.

Advantageous Effects of Invention

According to an MRI apparatus and a region imaging method of the present invention, reducing image quality deterioration due to static magnetic field inhomogeneity according to imaging conditions without increasing an operator workload is feasible.

BRIEF DESCRIPTION OF DRAWINGS

FIG. 12 is a flow chart showing a process flow of the practical example 6.
FIG. 13 is a functional block diagram of the practical example 7. Fig. (a) is a functional block diagram equivalent to the practical example 1, and Fig. (b) is a functional block diagram equivalent to the practical example 2.

DESCRIPTION OF EMBODIMENTS

Figure 1:
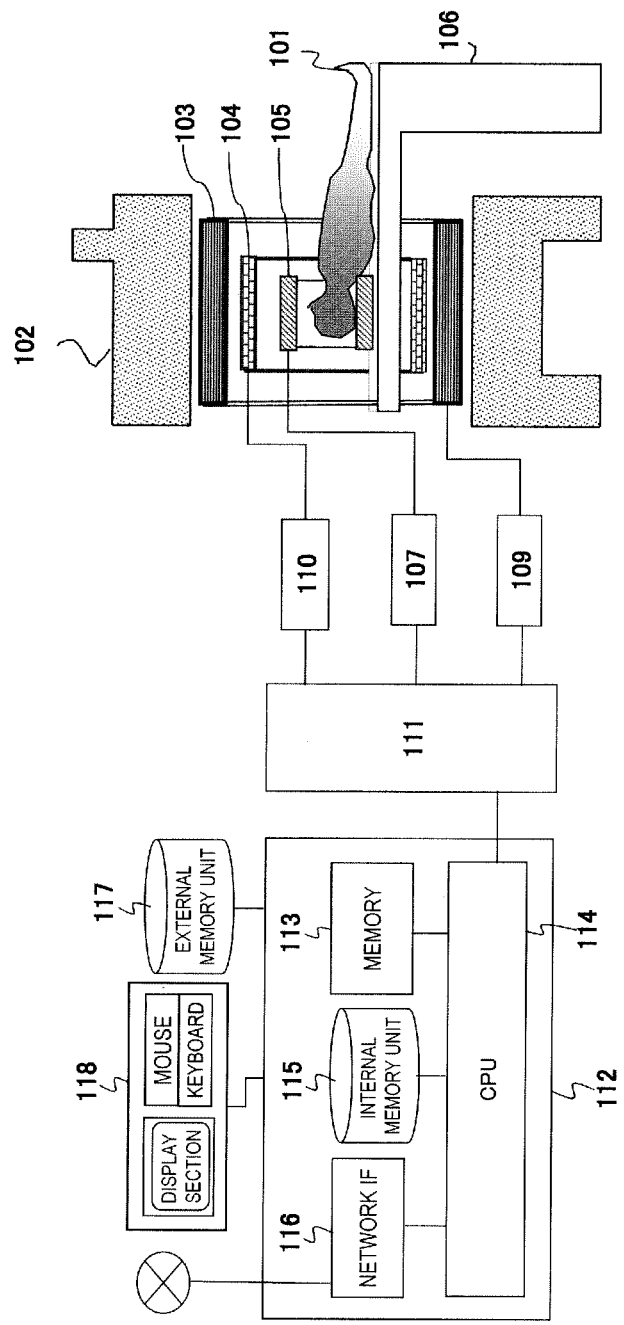
FIG. 1 is a block diagram showing the overall configuration for a practical example of an MRI apparatus of the present embodiment.

Hereinafter, a practical example desirable for an MRI apparatus of the present invention will be described in detail according to the attached figures. Additionally, in all the figures to explain practical examples of the invention, components having the same functions are denoted by the same reference numerals, and the explanation thereof will be omitted.

First, an MRI apparatus related to the present invention will be described based on FIG. 1. FIG. 1 is a block diagram showing the overall configuration for a practical example of an MRI apparatus related to the present embodiment.

The MRI apparatus obtains a tomographic image of the object 101 using the NMR phenomenon, as shown in FIG. 1, and is comprised by including the static magnetic field generation magnet 102, the gradient magnetic field coil 103, the gradient magnetic field power source 109, the RF transmission coil 104, the RF transmission unit 110, the RF receiving coil 105, the signal process unit 107, the measurement control unit 111, the overall control unit 112, the display and operation unit 118, and the bed 106 moving a top plate on which the object 101 is placed into and out of the inside of the static magnetic field generation magnet 102.

The static magnetic field generation magnet 102 generates a static magnetic field homogeneous in a direction orthogonal to the body axis of the object 101 in case of the vertical magnetic field method and in the body axis direction in case of the horizontal magnetic field method respectively, where a static magnetic field generation source of the permanent magnet method, normal conduction method, or superconducting method is disposed around the object 101.

The gradient magnetic field coil 103 is a coil wound in three axial directions of X, Y, and Z that are the real space coordinate system (coordinate system at rest) of an MRI apparatus. The respective gradient magnetic field coils are connected to the gradient magnetic field power source 109 that drives the coils to supply current. Specifically, the gradient magnetic field power source 109 of the respective gradient magnetic field coils is respectively driven by following a command from the measurement control unit 111 to be described to supply current to the respective gradient magnetic field coils. Hence, the gradient magnetic fields of Gx, Gy, and Gz are generated in three axial directions of X, Y, and Z.

When imaging a two-dimensional slice surface, a slice gradient magnetic field pulse (Gs) is applied in a direction orthogonal to a slice surface (imaging cross-section) to set a slice surface of the object 101, a phase encode gradient magnetic field pulse (Gp) and frequency encode (readout) gradient magnetic field pulse (Gf) is applied in the other two directions that are orthogonal to the slice surface and orthogonal with each other, and position information of the respective directions is encoded in an NMR signal (echo signal).

Also, in the gradient magnetic field coil 103, a shim coil generating a compensation magnetic field that reduces static magnetic field inhomogeneity by supplying shimming current is disposed. The shim coil is composed of component coils that generate a compensation magnetic field of the respective orders. Specifically, the second-order components ($x^2$, $y^2$, xy, yz, zx, ($x^2-y^2$) components, etc.) or higher-order components may be included. Additionally, the zero-order components (Bo components) are compensated by the excitation frequency f0 of an RF pulse, and the first-order components and a gradient magnetic field coil are combined.

The RF transmission coil 104 irradiates an irradiation RF magnetic field pulse (hereinafter, abbreviated as RF pulse) to the object 101 and is connected to the RF transmission unit 110 to supply high-frequency pulse current. Hence, an NMR phenomenon is induced by spin of atoms that comprise living tissue of the object 101. Specifically, in order to irradiate the RF pulse to the object 101, the RF transmission unit 110 is driven by following a command from the measurement control unit 111 to be described, performs amplitude modulation for a high-frequency pulse for amplification, and then supplies the pulse to the RF transmission coil 104 that is disposed in close proximity to the object 101.

The RF receiving coil 105 receives an echo signal emitted by an NMR phenomenon of spin that comprises living tissue of the object 101 and is connected to the signal process unit 107 to send the received echo signal to the signal process unit 107.

The signal process unit 107 performs detection process of an echo signal received in the RF receiving coil 105. Specifically, by following a command from the measurement control unit 111 to be described, the signal process unit 107 amplifies the received echo signal, orthogonal phase detection divides it into orthogonal two-system signals, the respective signals are sampled by the predetermined number (such as 128, 256, and 512), and the respective sampling signals are converted into a digital amount using A/D conversion. Therefore, the echo signal is obtained as time-series digital data of the predetermined number of sampling data (hereinafter, referred to as echo data). Then, the signal process unit 107 performs various processes for the echo data and sends the processed echo data to the measurement control unit 111.

The measurement control unit 111 is a control unit that controls mainly the gradient magnetic field power source 109, the RF transmission unit 110, and the signal process unit 107 by sending various commands for echo data collection required for reconstructing a tomographic image of the object 101. Specifically, the measurement control unit 111 is operated by control of the overall control unit 112 to be described, controls the gradient magnetic field power source 109, the RF transmission unit 110, and the signal process unit 107 based on control data in a predetermined sequence, repeats RF pulse irradiation and gradient magnetic field pulse application to the object 101 as well as echo signal detection from the object 101 in order to control echo data collection required for image reconstruction of an imaging region of the object 101. On the repetition, an application amount of a phase encode gradient magnetic field in case of two-dimensional imaging is changed in addition to an application amount of a slice encode gradient magnetic field in case of three-dimensional imaging. Per a single image, values of 128, 256, 512, etc. are normally selected for the number of phase encode, and values of 16, 32, 64, etc. are normally selected for the number of slice encode. Echo data from the signal process unit 107 is output to the overall control unit 112 by the control.

The overall control unit 112 controls the measurement control unit 111, performs control such as processing various data as well as displaying and saving process results, and is composed of the processing unit (CPU) 114, the memory 113, the internal memory unit 115 such as a magnetic disk, and the network IF 116 that performs an interface with an external network. Also, the overall control unit 112 may be connected to the external memory unit 117 such as an optical disk. Specifically, echo data is collected by controlling the measurement control unit 111 and is memorized in a region equivalent to a k space in the memory 113 based on encode information applied to echo data by the processing unit 114 when echo data is entered from the measurement control unit 111. Hereinafter, description stating that echo data is disposed in a k space represents that echo data is memorized in a region equivalent to a k space in the memory 113. Also, the echo data group memorized in a region equivalent to a k space in the memory 113 is referred to as k space data. Then, the processing unit 114 performs processes such as a signal process and image reconstruction by the Fourier transform for the k space, displays the consequent image of the object 101 on the display and operation unit 118 to be described, and then records the image in the internal memory unit 115 and external memory unit 117 as well as forwards the image an external device via the network IF 116.

The display and operation unit 118 is composed of a display unit that displays a reconstructed image of the object 101 and an operation unit such as a track ball, mouse, and keyboard to enter various control information of an MRI apparatus and control information of processes performed in the above overall control unit 112. The operation unit is disposed in close proximity to the display unit, and an operator controls various processes of the MRI apparatus interactively via the operation unit while checking the display unit.

A clinically predominant imaging target nuclide of an MRI apparatus is currently the hydrogen nucleus (proton) that is a main component material of the objects. By imaging spatial distribution of proton density and information about spatial distribution of relaxation time of an excitation state, forms and functions of the head, belly, limbs, etc. of human body are imaged two-dimensionally or three-dimensionally.

(Overview of the Region Imaging Method of the Present Invention)

The region imaging method related to the present invention includes the following steps. That is, static magnetic field inhomogeneity distribution that shows spatial distribution of static magnetic field inhomogeneity for a region including a region selected via an ROI setting (hereinafter, abbreviated as "selected region") is measured.

Then, a local Bo shimming current (C) of which static magnetic field inhomogeneity of a selected region is not small is calculated.

Then, shimming is performed for the selected region using the calculated local Bo shimming current (C) to calculate the post-adjustment excitation frequency (f0') that excites the selected region in a state where static magnetic field inhomogeneity of the selected region is reduced.

When imaging a selected region, either of frequency control where excitation is performed using an RF pulse of a post-adjustment excitation frequency (f0') after applying the calculated local Bo shimming current (C) to a shim coil to reduce static magnetic field inhomogeneity of the excitation region or phase control where excitation is performed by providing an increment (RF-Phase) during the irradiation phase equivalent to the post-adjustment excitation frequency (f0') to each RF pulse is performed. Additionally, the increment (RF-Phase) may be calculated directly from a frequency equivalent to static magnetic field inhomogeneity without being calculated from the post-adjustment excitation frequency (f0').

Specifically, the phase control calculates an increment (RF-Phase) during an irradiation phase of an RF pulse used for a pulse sequence based on static magnetic field inhomogeneity and changes the irradiation phase of the RF pulse for each increment (RF-Phase) in a state where static magnetic field inhomogeneity is reduced after shimming current is supplied to a shimming unit to control echo signal measurement. Also, the frequency control calculates shimming current based on static magnetic field inhomogeneity, calculates a post-adjustment excitation frequency of an RF pulse in a pulse sequence in a state where static magnetic field inhomogeneity is reduced after shimming current is supplied to a shimming unit, and calculates the shimming current and the post-adjustment excitation frequency for each selected region according to how plural selected regions overlap when settings for the plural selected regions are accepted to control echo signal measurement using the post-adjustment excitation frequency for an RF pulse in a pulse sequence.

The practical examples 1 and 2 are examples for phase control, the practical examples 3 to 6 are examples for frequency control, and the practical examples 7 and 8 are examples for using both of the phase control and frequency control.

Hereinafter, calculation methods for a post-adjustment excitation frequency (f0') to perform frequency control and RF-Phase to perform phase control will be described.

(Calculating a Post-Adjustment Excitation Frequency)

The overview of a calculation method for a post-adjustment excitation frequency with consideration for static magnetic field inhomogeneity will be described.

First, static magnetic field inhomogeneity distribution in a region including a selected region is measured. For example, a dual echo Gradient Echo sequence of an excitation frequency f0 can be used for measuring static magnetic field inhomogeneity distribution. Taking a phase image obtained from the first echo signal as $\phi 1$, a phase image obtained from the second echo signal as $\phi 2$, and a time interval between a peak of the first echo signal and a peak of the second echo signal as $\tau$, static magnetic field inhomogeneity distribution is expressed as the formula (1). In addition, static magnetic field inhomogeneity is represented using a frequency in the present description.

$$\Delta B0=(\phi 2-\phi 1)/2\pi\tau \qquad (1)$$

Next, for the static magnetic field inhomogeneity distribution calculated using the formula (1), a mask process is performed so that only an exciting selected region is targeted to calculate a local Bo shimming current (C) that reduces static magnetic field inhomogeneity in the selected region. Specifically, for a selected region, when taking a character matrix in which a shim coil character measured at the installation of an MRI apparatus is reflected as A and a shim coil current value as C (=[$\Delta$f0, Gx, Gy, Gz, Gxy]), a matrix of the formula (2) is solved for C.

$$A \cdot B = \Delta B0 \qquad (2)$$

Here, $\Delta$f0 is a frequency offset. Gx, Gy, and Gz are the first-order compensation magnetic field components that the first-order shim coils x, y, and z generate respectively. In addition, because the first-order shim coil is normally used also as a gradient magnetic field coil, current to generate the first-order compensation magnetic field is supplied to the gradient magnetic coil. On the other hand, Gxy is the second-order compensation magnetic field component that the second-order shim coil xy generates. Although only xy is described as a term of the second-order or higher, higher-order terms such as $x^2$, $y^2$, yz, zx, and ($x^2$-$y^2$) may be generally included.

Next, in a state where static magnetic field inhomogeneity is reduced after shimming is performed for a selected region using a local Bo shimming current (C) calculated above, a post-adjustment excitation frequency (f0') that is an excitation frequency of an RF pulse to excite the selected region is determined by the formula (3).

$$f0'=f0+\Delta f0+<f0> \qquad (3)$$

Here, f0 is an excitation frequency of a dual echo Gradient Echo used when measuring static magnetic field inhomogeneity distribution, $\Delta$f0 is a frequency offset calculated from the formula (2), <f0> a frequency offset calculated based on a static magnetic field inhomogeneity estimation map after shimming. That is, a post-adjustment excitation frequency (f0') of an RF pulse that excites a selected region is calculated based on a state where static magnetic field inhomogeneity is reduced and is the one in which a frequency ($\Delta$f0+<f0>) corresponding to static magnetic field inhomogeneity is added to an excitation frequency of an RF pulse used when measuring static magnetic field inhomogeneity distribution. A static magnetic field inhomogeneity estimation map after shimming is calculated by adding a magnetic field generated when shim coil current values [Gx, Gy, Gz, Gxy] are applied to $\Delta$B0. To calculate <f0>, for example, averages of maximum values and minimum values in a static magnetic field inhomogeneity estimation map after shimming in a selected region, an arithmetic average in a static magnetic field inhomogeneity estimation map in a selected region, a histogram average in a static magnetic field inhomogeneity estimation map in a selected region, etc. are used.

(RF-Phase Calculation)

Next, a calculation method of RF-Phase that is an increment for each irradiation of an irradiation phase of an RF pulse equivalent to a post-adjustment excitation frequency (f0') of the formula (3) will be described.

In an SSFP sequence, an RF pulse in which a flip angle is fixed is irradiated continuously for a certain repetition time TR. In this case, an irradiation phase is increased in increments of 180 degrees. Taking an excitation frequency in an SSFP sequence as f0, because a spin excited at a post-adjustment excitation frequency (f0') derived from the formula (3) rotates by (f0'-f0)*TR*360[deg.] during TR, the same behavior is performed as in the case of taking RF-Phase as 180+(f0'-f0)*TR*360.

Therefore, the following formula is used to convert a post-adjustment excitation frequency (f0') calculated using the formula (3) to RF-Phase.

$$RF\text{-Phase} = [180 + 360^*TR^*(f0' - f0)] \, \%360 \qquad (4)$$
$$= [180 + 360^*TR^*(\Delta f0 + <f0>)] \, \%360$$

% represents a remainder operator, an operation of A % B means a remainder when dividing A by B. That is, RF-Phase is a phase amount where phase rotation equivalent to a frequency amount ($\Delta$f0+<f0>) corresponding to static magnetic field inhomogeneity is provided to an irradiation phase of an RF pulse. Using the formula (4), it is understood that RF-Phase can be calculated not only via calculation for a post-adjustment excitation frequency (f0') but also directly from a frequency amount ($\Delta$f0+<f0>) corresponding to static magnetic field inhomogeneity. At this point, f0 that is an actual excitation frequency in an SSFP sequence may be automatically set to a peak frequency of a water spectrum and may be also set by adjusting manually from the above spectrum shape by an operator after measuring a spectrum of an image slice cross-section as a previous measurement (pre-scan). f0' is an excitation frequency calculated using the formula (3).

Thus, by irradiating an RF pulse in an SSFP sequence while changing the irradiation phase by an increment (RF-Phase) calculated using the formula (4) when irradiating for each repetition time TR, even if an actual excitation frequency is f0, the excitation frequency has an effect equivalent to f0'. Moreover, because a position of band artifacts is controlled by RF-Phase, by controlling RF-Phase, even if an actual excitation frequency (f0) is changed, the position of band artifacts can be fixed or can be moved to a desirable position.

(Flow Chart for Control Method Selection)

Figure 2:
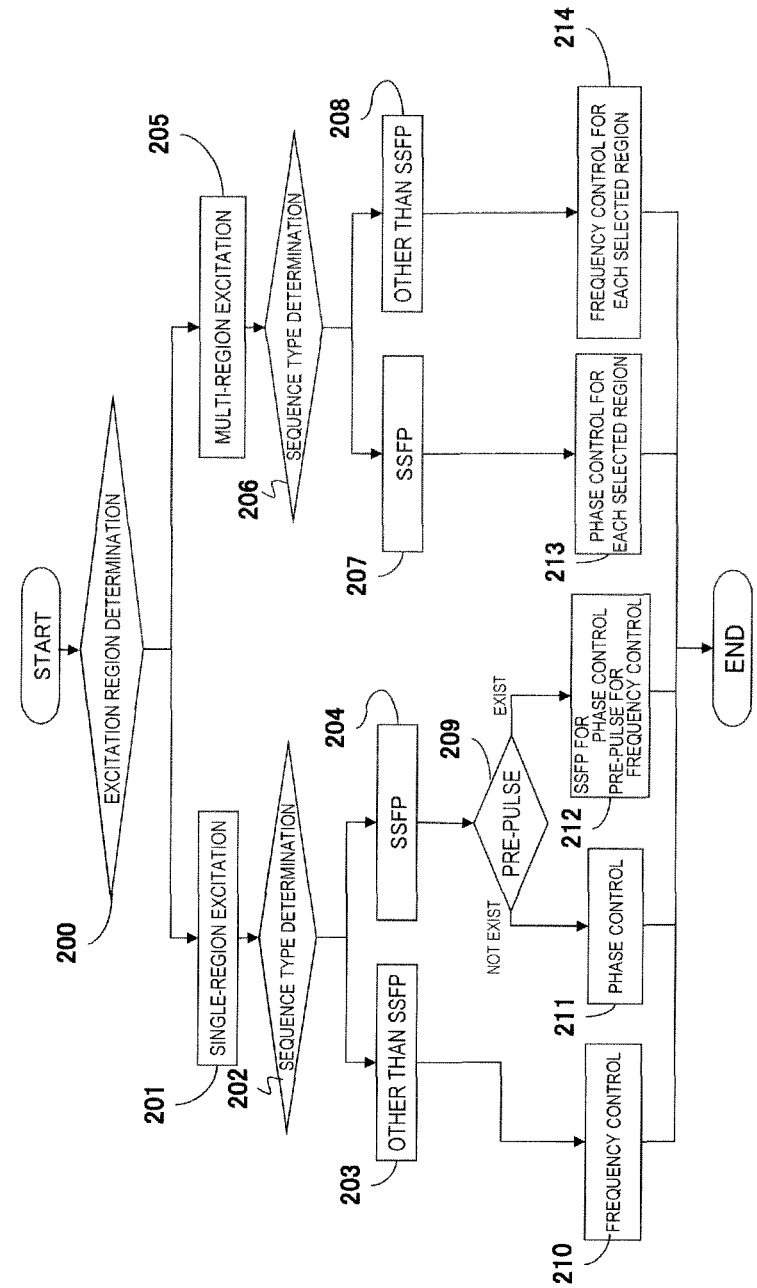
FIG. 2 is a flow chart showing a process flow to select a control method according to an imaging parameter.

An MRI apparatus and a region imaging method of the present invention perform either of the above phase control or frequency control according to imaging parameters as imaging conditions. Imaging parameters related to control method selection include the number of selected regions and a sequence type of an imaging sequence. In a case where an imaging sequence is comprised of a main sequence that measures an echo signal for an image and a pre-pulse sequence that precedes the main sequence, the sequence type means that for the main sequence. A process flow for performing control method selection according to those imaging parameters will be described based on the flow chart in FIG. 2.

In Step 200, the computing process unit 114 judges whether a selected region set by an operator is a single region or multiple regions.

In case of a single region, a main sequence and the pre-pulse sequence or another main sequence excites only the same region together.

On the other hand, in case of multiple regions, a main sequence and the pre-pulse sequence or another main sequence excites different regions respectively. The single-region case 201 proceeds to Step 202, and the multi-region case 205 proceeds to Step 206.

In Step 202 and 206, the computing process unit 114 judges whether a sequence type is SSFP or the other.

In case of single-region excitation and other than an SSFP sequence (203), a shimming current value and an excitation frequency are calculated using publicly known technique described in NPTL 1 to generate an imaging sequence (210).

In case of single-region excitation and an SSFP sequence (204), in Step 209, the computing process unit 114 judges whether a pre-pulse sequence is used in combination or not. If a pre-pulse sequence is not used in combination, a local Bo shimming current value and RF-Phase in an SSFP sequence are calculated using the following practical example 1 or 2 to generate an imaging sequence (211). If a pre-pulse sequence is used in combination, using the practical example 7, a local Bo shimming current value and a post-adjustment excitation frequency in a pre-pulse sequence are calculated, and then a local Bo shimming current value and RF-Phase in an SSFP sequence are calculated to generate an imaging sequence (212).

In case of multi-region excitation and other than an SSFP sequence (208), using any of the following practical examples 3 to 6, a local Bo shimming current value and a post-adjustment excitation frequency for the each region are calculated according to how excitation regions overlap to generate an imaging sequence (214).

In case of multi-region excitation and an SSFP sequence (207), using the following practical example 8, a local Bo shimming current value and a post-adjustment excitation frequency in a pre-pulse sequence are calculated according to how excitation regions overlap, and then a local Bo shimming current value and RF-Phase in an SSFP sequence are calculated to generate an imaging sequence (213).

The practical example 1 for an MRI apparatus and a region imaging method of the present invention will be described. The present practical example 1 calculates local Bo shimming current applied to a shim coil and an increment (RF-Phase) of an RF pulse according to static magnetic field inhomogeneity, and then imaging is performed using the calculated local Bo shimming current and RF-Phase. Hereinafter, the present practical example 1 will be described in detail based on FIGS. 3(a) and 4.

(Functional Block of the Practical Example 1)

First, the respective functions of the computing process unit 114 to achieve a region imaging method of the practical example 1 will be described based on a functional block diagram shown in FIG. 3(a). The computing process unit 114 related to the practical example 1 is comprised of the region selection unit 301, the static magnetic field inhomogeneity measurement unit 302, the local Bo shimming current calculation unit 303, the excitation frequency calculation unit 304, the RF-Phase calculation unit 305, and the setting unit 306.

The region selection unit 301 displays a layout image on the display and operation unit 118 and accepts the ROI setting input for operator's region selection. A selected region with the ROI set is set as an imaging region. Then, layout information of the selected region is notified to the static magnetic field inhomogeneity measurement unit 302 and the local Bo shimming current calculation unit 303.

The static magnetic field inhomogeneity measurement unit 302 generates control data in a measuring sequence for measuring static magnetic field inhomogeneity distribution of a region including a selected region to notify to the measurement control unit 111, and then controls measurement of static magnetic field inhomogeneity distribution of a region including a selected region. Then, the measurement control unit 111 starts a static magnetic field inhomogeneity distribution measurement sequence, and then notifies measured echo data to the local Bo shimming current calculation unit 303. In a static magnetic field inhomogeneity distribution measurement sequence, the dual echo Gradient Echo sequence can be used as described above.

The local Bo shimming current calculation unit 303 calculates local Bo shimming current (C) that reduces static magnetic field inhomogeneity of a selected region. Therefore, first, in order to extract static magnetic field inhomogeneity distribution of a selected region, a mask process is performed for static magnetic field inhomogeneity distribution of a region including a selected region. Next, local Bo shimming current (C) that reduces static magnetic field inhomogeneity of a selected region is calculated. The details for calculating local Bo shimming current (C) are as described before. Then, calculated local Bo shimming current (C) is notified to the excitation frequency calculation unit 304 and the setting unit 306.

The excitation frequency calculation unit 304 calculates a post-adjustment excitation frequency (f0') to excite the selected region using local Bo shimming current (C) so that static magnetic field inhomogeneity of a selected region is reduced. The details for calculating the post-adjustment excitation frequency (f0') are as described before.

The RF-Phase calculation unit 305 calculates RF-Phase as a phase rotation amount corresponding to a post-adjustment excitation frequency (f0') calculated in the excitation frequency calculation unit 304. Alternatively, RF-Phase is calculated as a phase rotation amount equivalent to a frequency amount ($\Delta f0 + <f0>$) corresponding to static magnetic field inhomogeneity. The details for calculating RF-Phase are as described before. Then, RF-Phase is notified to the setting unit 306.

The setting unit 306 sets local Bo shimming current (C) calculated in the local Bo shimming current calculation unit 303, RF-Phase calculated in the RF-Phase calculation unit 305, and an actual post-adjustment excitation frequency (f0') as local Bo shimming current, RF-Phase, and an excitation frequency in the selected region. Then, control data in an imaging sequence is generated using these set local Bo shimming current (C), RF-Phase, and an excitation frequency (f0') and is notified to the measurement control unit 111.

(Process Flow of the Practical Example 1)

Next, a process flow of the practical example 1 for which the above respective functional units cooperate with each other will be described based on the flow chart shown in FIG. 4. The present process flow is memorized in the internal memory unit 115 as a program in advance and is executed by the processing unit 114 reading the program from the internal memory unit 115. Hereinafter, process contents of the respective process steps will be described in detail.

In Step 400, the region selection unit 301 displays a layout image on the display and operation unit 118 and accepts the ROI setting input for operator's region selection. Then, layout information of the selected region selected in ROI is notified to the static magnetic field inhomogeneity measurement unit 302.

In Step 401, the static magnetic field inhomogeneity measurement unit 302 measures static magnetic field inhomogeneity distribution of a region including the above selected region. The details are as described before.

In step 402, the local Bo shimming current calculation unit 303 performs a mask process so that only a selected region is selected for static magnetic field inhomogeneity distribution measured in Step 401. Then, local Bo shimming current (C) that reduces static magnetic field inhomogeneity of a selected region is calculated. The details are as described before.

In Step 403, the excitation frequency calculation unit 304 calculates a post-adjustment excitation frequency (f0') so that static magnetic field inhomogeneity is reduced. The details are as described before.

In Step 404, the RF-Phase calculation unit 305 calculates RF-Phase corresponding to a post-adjustment excitation frequency (f0') calculated in Step 403. The details are as described before.

In Step 405, the setting unit 306 respectively sets local Bo shimming current (C) calculated in Step 402, RF-Phase calculated in Step 404, and an actual excitation frequency (f0) used in calculation in Step 404 as local Bo shimming current, RF-Phase, and an excitation frequency for when a selected region is excited, generates control data of an imaging sequence to be described later, and then notifies to the measurement control unit 111.

In Step 406, the measurement control unit 111 applies phase control that changes an irradiation phase of an RF pulse by an increment using local Bo shimming current (C), RF-Phase, and an excitation frequency (f0) set in Step 405 to control imaging.

Additionally, calculation for RF-Phase in Step 404 does not use a post-adjustment excitation frequency (f0'), and RF-Phase may be calculated as a phase rotation amount equivalent to an frequency amount ($\Delta f0 + <f0>$) corresponding to static magnetic field inhomogeneity calculated from static magnetic field inhomogeneity distribution measured in Step 401 and local Bo shimming current (C) calculated in Step 402. In this case, calculation for a post-adjustment excitation frequency (f0') in Step 403 is omitted.

Also, in case of imaging multiple selected regions, multiple selected regions are set by multiple ROI settings in Step 400, static magnetic field inhomogeneity distribution of a region including multiple selected regions in Step 401 is calculated, and then Steps 402 to 406 will be repeated for each selected region. Alternatively, the practical example 8 to be described later will be executed.

These are the descriptions of the process flow of the present practical example 1.

As described above, an MRI apparatus and a region imaging method of the present practical example 1 calculates an increment (RF-Phase) of an irradiation phase of an RF pulse used in a pulse sequence based on static magnetic field inhomogeneity, applies phase control that changes an irradiation phase of an RF pulse by an increment in a state where static magnetic field inhomogeneity is reduced after shimming current is supplied to a shimming unit to control echo signal measurement. Consequently, image quality deterioration can be reduced caused by static magnetic field inhomogeneity distribution. Also, because a position of band artifacts is controlled by RF-Phase, the position of band artifacts is not changed and can be fixed at the same position even if an operator changes an excitation frequency (f0).

Practical Example 2

Next, the practical example 2 for an MRI apparatus and a region imaging method of the present invention will be described. In the above practical example 1, although appropriate RF-Phase is calculated automatically, band artifacts are mixed in ROI in a case where static magnetic field inhomogeneity in ROI is 1/TR [Hz] or more. In the practical example 2, an operator is enabled to adjust a position of band artifacts easily in such case. Specifically, although the overview of the process flow to set local Bo shimming current and a post-adjustment excitation frequency (f0') is the same as the above practical example 1, a position of the band artifacts can be adjusted by calculating an increment (RF-Phase) after a phase of operator's setting input is added.

Hereinafter, mainly with a focus on differences from the above practical example 1, the present practical example 2 will be described in detail.

(Calculation for an Adjustment Value of RF-Phase)

First, an overview of an increment (RE-Phase) calculation method in a case where an operator adjusts a position of band artifacts will be described.

First, the graphical user interface (GUI) to be displayed on the display and operation unit 118 that is an input screen for an adjustment value of RF-Phase will be described using FIG. 5. The GUI is comprised of the RF-Phase display unit 501 that displays an RF-Phase value calculated from the formula (4) described in the above practical example 1 and the adjustment value input unit 502 where an adjustment value φ of RF-Phase is input by an operator as shown in FIG. 5(a). However, if an RF-Phase value is not required, as shown in FIG. 5(b), an explicit display (for example, "Auto") showing that an automatically adjusted value is used may be displayed on the RF-Phase display unit 501.

First, an operator manually inputs and sets an adjustment value of RF-Phase in the adjustment value input unit 502 of the above GUI.

Next, after measuring static magnetic field inhomogeneity distribution, local Bo shimming current (C) for a selected region and a post-adjustment excitation frequency (f0') that reduces band artifacts of a selected region are calculated respectively. The calculation method is the same as the above practical example 1.

Finally, by adding an adjustment value φ set by an operator to RF-Phase (that is, RF-Phase calculated using the formula (4) of the practical example 1) corresponding to a post-adjustment excitation frequency (f0'), RF-Phase is calculated based on the following formula (5).

$$RF\text{-Phase} = [180 + \phi + 360^* TR^*(f0' - f0)] \, \%360 \quad (5)$$
$$= [180 + \phi + 360^* TR^*(\Delta f0 + <f0>)] \, \%360$$

Here, the respective variables are the same as the formula (4). Even in this case, as shown in the formula (5), by adding an adjustment value φ set by an operator to a phase rotation amount of equivalent to a frequency amount ($\Delta f0 + <f0>$)

corresponding to static magnetic field inhomogeneity, RF-Phase may be calculated without using a post-adjustment excitation frequency (f0') similarly to the above practical example 1.

The subsequent process is the same as the practical example 1.

(Functional Block of the Practical Example 2)

Figure 3:
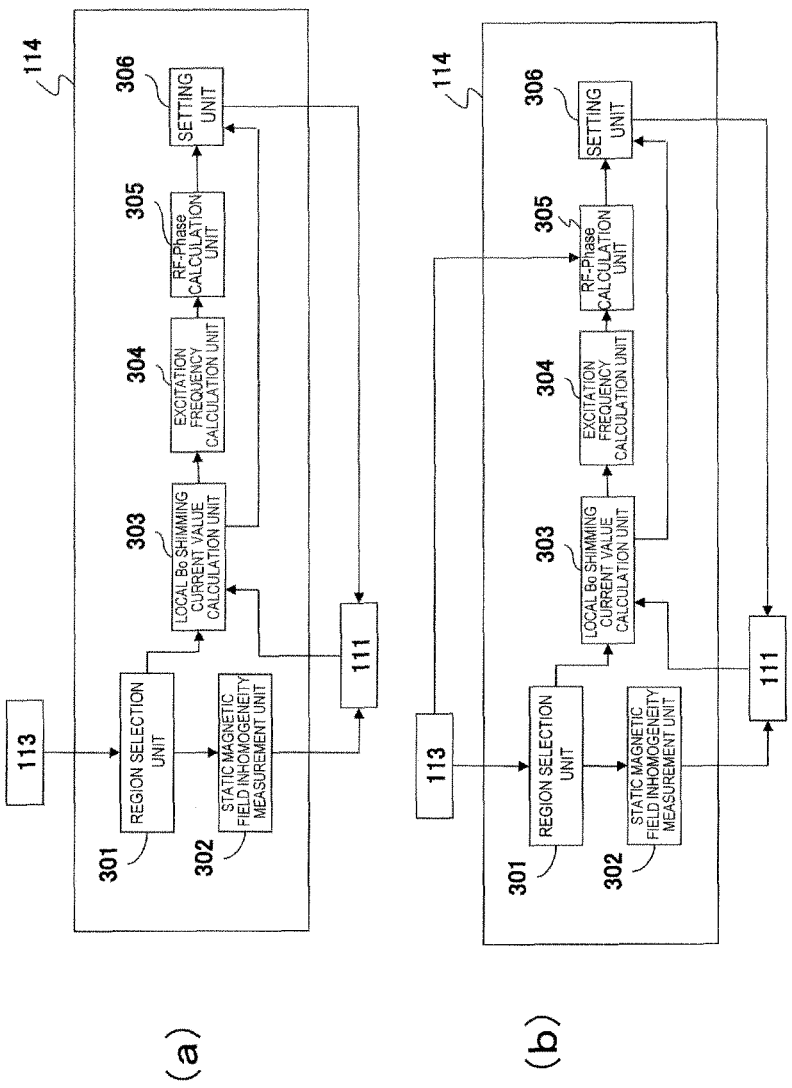
In FIG. 3, Fig. (a) is a functional block diagram of the practical example 1, and Fig. (b) is a functional block diagram of the practical example 2.

Next, respective functions of the processing unit 114 to achieve a region imaging method of the present practical example 2 will be described based on FIG. 3(*b*). Although the functional block of the processing unit 114 related to the present practical example 2 is basically the same as the above practical example 1, the function of the RF-Phase calculation unit 305 varies. Hereinafter, only differences from the above practical example 1 will be described, and the same descriptions will be omitted.

The RF-Phase calculation unit 305 calculates RF-Phase using an adjustment value $\phi$ of RF-Phase. Specifically, RF-Phase is calculated using the formula (5) based on a post-adjustment excitation frequency (f0') calculated in the excitation frequency calculation unit 304 and an adjustment value $\phi$ of RF-Phase set and input by an operator via the adjustment value input unit 502 displayed on the display and operation unit 118. In other words, RF-Phase is calculated based on RF-Phase corresponding to a post-adjustment excitation frequency (f0') calculated in the excitation frequency calculation unit 304 and an adjustment value $\phi$ of RF-Phase. Alternatively, RF-Phase is calculated using the formula (5) based on a phase rotation amount equivalent to a frequency amount ($\Delta f0 + <f0>$) corresponding to static magnetic field inhomogeneity and an adjustment value $\phi$ of RF-Phase set and input by an operator. Then, a calculated RF-Phase is notified to the setting unit 306.

(Process Flow of the Practical Example 2)

Next, a process flow of the practical example 2 that the above respective functional units for which the above respective functional units cooperate with each other will be described based on the flow chart shown in FIG. 4. Although the process flow of the practical example 2 is basically the same as the process flow in FIG. 4 described in the above practical example 1, the process contents of Step 404 varies. Hereinafter, only differences from the above practical example 1 will be described, and the same descriptions will be omitted.

Figure 5:
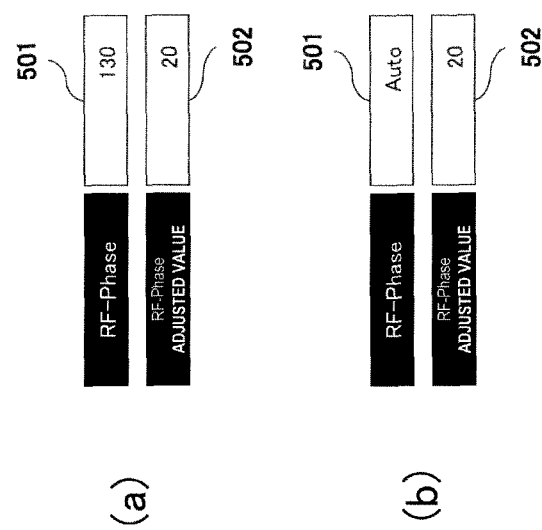
FIG. 5 is a diagram showing a graphical user interface (GUI) displayed on the display and operation unit 118 that is a screen to enter an RF-Phase adjustment value.

In Step 404, the RF-Phase calculation unit 305 displays GUI shown in FIG. 5 on the display and operation unit 118 and accepts an adjustment value $\phi$ of RF-Phase that an operator inputs and sets. Then, RF-Phase is calculated based on a post-adjustment excitation frequency (f0') calculated in the excitation frequency calculation unit 304 and an adjustment value $\phi$ of RF-Phase. Alternatively, RF-Phase is calculated based on a phase rotation amount equivalent to a frequency amount ($\Delta f0 + <f0>$) corresponding to static magnetic field inhomogeneity and an adjustment value $\phi$ of RF-Phase set and input by an operator. The details are as described before.

Also, in case of imaging multiple selected regions, multiple selected regions are set by multiple ROI settings in Step 400 similarly to the practical example 1, static magnetic field inhomogeneity distribution of a region including multiple selected regions is calculated in Step 401, and Steps 402 to 406 will be repeated for each selected region. Alternatively, the practical example 8 to be described later will be executed.

These are the descriptions of the process flow of the present practical example 2.

As described above, an MRI apparatus and a region imaging method of the present practical example 2 enables an operator to adjust a position of band artifacts easily by calculating RF-Phase after the operator adds an adjustment value of RF-Phase to an increment (RF-Phase) calculated according to static magnetic field inhomogeneity distribution. Also, because the position of the band artifacts is controlled by RF-Phase similarly to the above practical example 1, the position of the band artifacts is not changed and can be fixed at the same position even if the operator changes an excitation frequency (f0).

Practical Example 3

Figure 6:
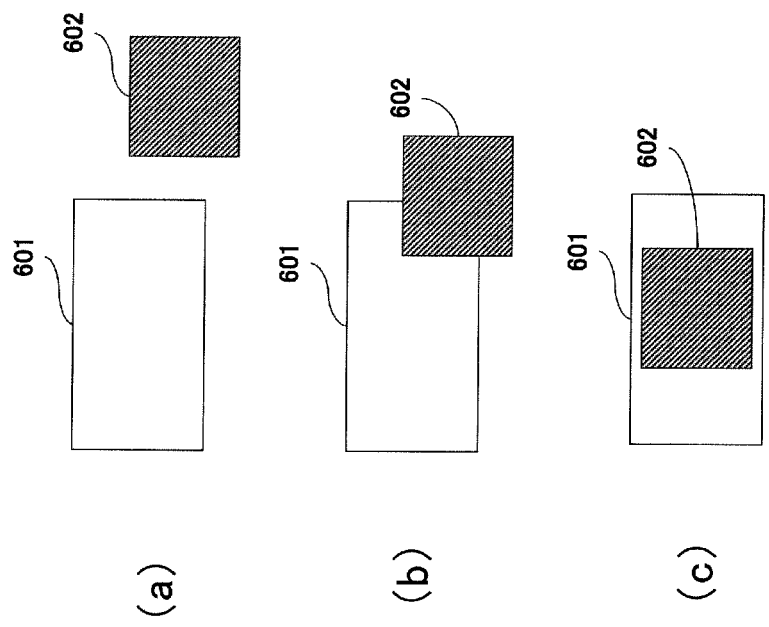
FIG. 6 is a diagram showing an example of how two selected regions overlap.

The practical example 3 for an MRI apparatus and a region imaging method of the present invention will be described. In the present practical example 3, local Bo shimming current and a post-adjustment excitation frequency to be applied to a shim coil are calculated for each region, and then imaging is performed for each region sequentially. Therefore, the present practical example 3 is suitable for imaging when the selected region 1 and selected region 2 in FIG. 6(*a*) do not have a common region or when the selected region 1 and selected region 2 in FIG. 6(*b*) have a common region. In other words, the present practical example 3 is suitable for when two regions do not overlap at least partially with each other. Additionally, in the present practical example 3, a common region where two regions overlap will be imaged twice. Hereinafter, the present practical example 3 will be described in detail based on FIGS. 7 and 8.

(Functional Block of the Practical Example 3)

First, the respective functions of the processing unit 114 to achieve a region imaging method of the present practical example 3 will be described based on the functional block diagram shown in FIG. 7. The functional block of the processing unit 114 related to the present practical example 3 is comprised by including not the RF-Phase calculation unit 305 but the determination unit 705 compared to the block diagram shown in FIG. 3(*a*) described in the above practical example 1. Hereinafter, only differences from the functional block diagram in the above practical example 1 will be described, and descriptions of the same contents will be omitted.

The region selection unit 301 is similar to the practical example 1.

The static magnetic field inhomogeneity measurement unit 302 is similar to the practical example 1. The local Bo shimming current calculation unit 303 calculates local Bo shimming current (C) that reduces static magnetic field inhomogeneity in a selected region. The details for calculating local Bo shimming current (C) are similar to the practical example 1.

The excitation frequency calculation unit 304 sets a post-adjustment excitation frequency (f0') to excite a selected region so that static magnetic field inhomogeneity in the selected region is reduced. The details for calculating a post-adjustment excitation frequency (f0') are similar to the practical example 1.

The determination unit 705 determines whether distribution in the selected region of static magnetic field inhomogeneity distribution (i.e., a static magnetic field inhomogeneity estimation map after shimming) for when local Bo shimming current (C) and a post-adjustment excitation frequency (f0') calculated for a selected region are used fulfills predetermined criteria or not. The determination criteria are that the distribution is a threshold value (100 Hz) or less, that a difference between the maximum value and the minimum value is a threshold value or less, etc. for static magnetic field inhomogeneity distribution in a selected region on a static magnetic field inhomogeneity estimation map after shimming. Then, local Bo shimming current (C) and a post-adjustment excitation frequency (f0') that fulfill the determination criteria are notified to the setting unit 306.

The setting unit 306 sets local Bo shimming current (C) and a post-adjustment excitation frequency (f0') where static magnetic field inhomogeneity distribution in a selected region fulfills the predetermined criteria as local Bo shimming current and an excitation frequency in the selected region. Then, control data is generated in an imaging sequence using these local Bo shimming current (C) and a post-adjustment excitation frequency (f0') that were set, and then the control data is notified to the measurement control unit 111.

(Process Flow of the Practical Example 3)

Figure 8:
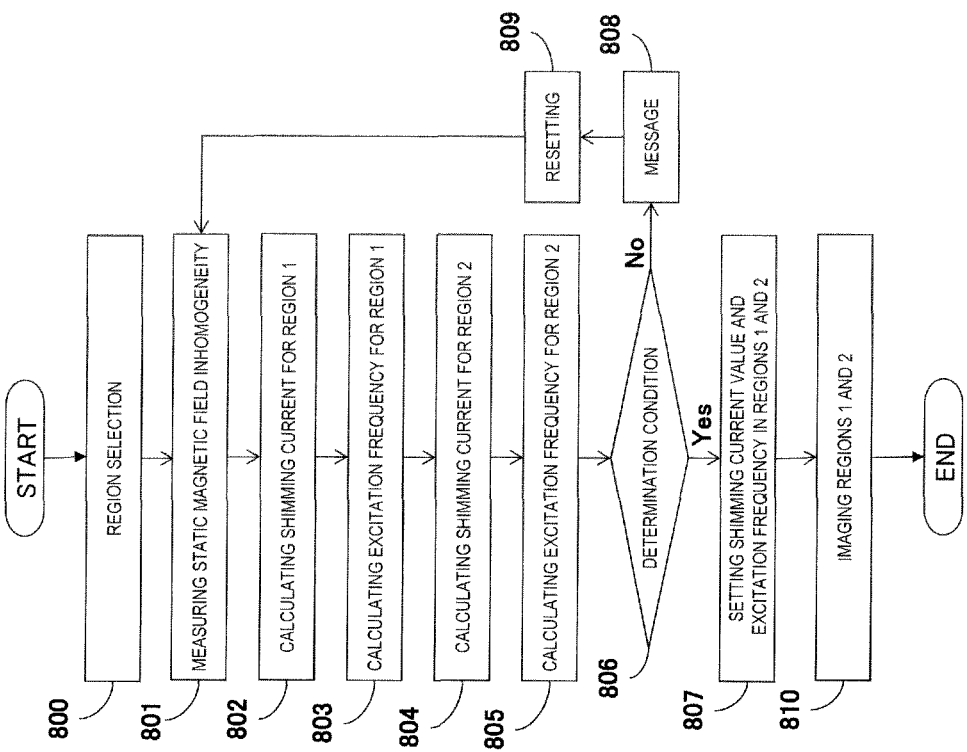
FIG. 8 is a flow chart showing a process flow of the practical example 3.

Next, the process flow of the present practical example 3 for which the above respective functional units cooperate with each other will be described based on the flow chart shown in FIG. 8. The present process flow is memorized as a program in advance in the internal memory unit 115 and is executed by the processing unit 114 reading the program from the internal memory unit 115. Hereinafter, the process contents of the respective process steps will be described in detail.

In Step 800, the region selection unit 301 displays a layout image on the display and operation unit 118 and accepts each ROI setting input for operator's region selection for the selected region 1 and selected region 2. Then, layout information of the selected region 1 and selected region 2 that were selected is notified to the static magnetic field inhomogeneity measurement unit 302.

In Step 801, the static magnetic field inhomogeneity measurement unit 302 measures static magnetic field inhomogeneity distribution in a region that includes the selected region 1 and selected region 2. The details are as described before.

In Step 802, the local Bo shimming current calculation unit 303 performs a mask process so that only the selected region 1 is selected for the static magnetic field inhomogeneity distribution measured in Step 801. Then, local Bo shimming current ($C_1$) that reduces static magnetic field inhomogeneity in the selected region 1 that was selected is calculated. The details are as described before.

In Step 803, the excitation frequency calculation unit 304 sets a post-adjustment excitation frequency ($f0_1'$) in the selected region 1 so that static magnetic field inhomogeneity of the selected region 1 is reduced. The details are as described before.

In Step 804, the local Bo shimming current calculation unit 303 performs a mask process so that only the selected region 2 is selected for the static magnetic field inhomogeneity distribution measured in Step 801. Then, local Bo shimming current ($C_2$) that reduces static magnetic field inhomogeneity in the selected region 2 that was selected is calculated. The details are as described before.

In Step 805, the excitation frequency calculation unit 304 sets a post-adjustment excitation frequency ($f0_2'$) in the selected region 2 so that static magnetic field inhomogeneity of the selected region 2 is reduced. The details are as described before.

In Step 806, the determination unit 705 determines whether static magnetic field inhomogeneity distribution (i.e., a static magnetic field inhomogeneity estimation map after shimming) in the selected region 1 and selected region 2 for when local Bo shimming current ($C_1$ and $C_2$) calculated in Steps 802 and 804 as well as a post-adjustment excitation frequency ($f0_1'$ and $f0_2'$) calculated in Steps 803 and 805 are used fulfills predetermined criteria or not. The evaluation criteria are as described before. If the evaluation criteria are fulfilled (Yes), the procedure proceeds to Step 807; if not (No), the procedure proceeds to Step 808.

In Step 807, the setting unit 306 sets local Bo shimming current ($C_1$) calculated in Step 802 and a post-adjustment excitation frequency ($f0_1'$) calculated in Step 803 respectively as local Bo shimming current and an excitation frequency for exciting the selected region 1, generates control data in an imaging sequence to be described later, and then notifies the control data to the measurement control unit 111. Similarly, the setting unit 306 sets local Bo shimming current ($C_2$) calculated in Step 804 and a post-adjustment excitation frequency ($f0_2'$) calculated in Step 805 respectively as local Bo shimming current and an excitation frequency for exciting the selected region 2, generates control data in an imaging sequence to be described later, and then notifies the control data to the measurement control unit 111.

In Step 808, the determination unit 705 displays a warning and beeps on the display and operation unit 118 when imaging conditions have to be changed due to that determination conditions are not fulfilled.

In Step 809, an operator performs settings such as an imaging parameter again so that static magnetic field inhomogeneity distribution in the selected region 1 and selected region 2 fulfills predetermined determination criteria. For example, re-adjustment of the selected region 1 and selected region 2, TR extension in case of an SSFP sequence, and re-adjustment of excitation positions in case of a pencil beam are performed. Then, the procedure proceeds to Step 801 to measure static magnetic field inhomogeneity distribution again, and processes in the above respective steps are repeated.

In Step 810, the measurement control unit 111 controls excitation of the selected region 1 and selected region 2 using local Bo shimming current ($C_1$, $C_2$) calculated in Step 804 and a post-adjustment excitation frequency ($f0_1'$, $f0_2'$) of the selected region 1 and selected region 2 set in Step 807.

Figure 9:
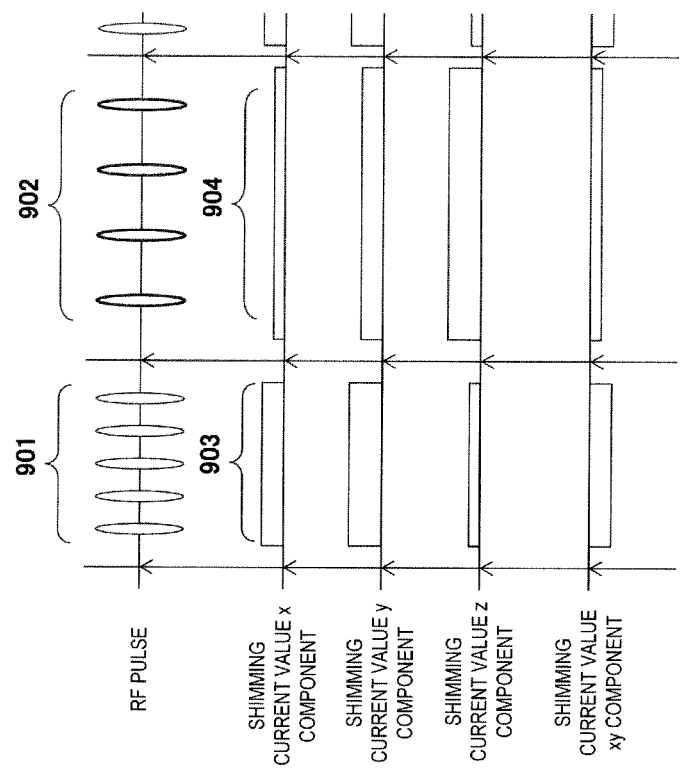
FIG. 9 is a sequence chart of the practical example 3.

For example, when using an imaging sequence shown in a sequence chart in FIG. 9, according to an imaging parameter of the selected region 1, a post-adjustment excitation frequency ($f0_1'$) and local Bo shimming current ($C_1$) are set to start excitation of the selected region 1. At the same time, an actual excitation frequency of the respective RF pulses such as slice selection is calculated using a set post-adjustment excitation frequency ($f0_1'$). Then, while set local Bo shimming current ($C_1$) is applied to the respective shim coils (903), an RF pulse of the calculated respective excitation frequencies (901) is irradiated.

When excitation of the selected region 1 is completed, according to an imaging parameter of the selected region 2, a post-adjustment excitation frequency ($f0_2'$) and local Bo shimming current ($C_2$) are set to start excitation of the selected region 2. At the same time, similarly to the selected region 1, an actual excitation frequency of the respective RF pulses such as slice selection is calculated using a set post-adjustment excitation frequency ($f0_2'$). Then, while set local Bo shimming current ($C_2$) is applied to the respective shim coils (904), an RF pulse of the calculated respective excitation frequencies (902) is irradiated.

Additionally, although only xy components are displayed as higher-order components of the second-order of local Bo shimming current in the present sequence chart, higher-order terms such as yz, zx, and (x^2-y^2) may be included generally.

These are the descriptions of the process flow of the present practical example 3.

As described above, an MRI apparatus and a region imaging method in the present practical example 3 calculates local Bo shimming current and a post-adjustment excitation frequency according to the static magnetic field inhomogeneity for each selected region and excites the respective regions by changing local Bo shimming current and a post-adjustment excitation frequency for each selected region. Consequently, when a plurality of selected regions are separately excited and imaged, local Bo shimming current and a post-adjustment excitation frequency that are optimum according to static magnetic field inhomogeneity for each selected region are used, which can reduce image quality deterioration caused by static magnetic field inhomogeneity distribution for each selected region.

Practical Example 4

Next, the practical example 4 for an MRI apparatus and a region imaging method of the present invention will be described. Generally, a response time of local Bo shimming current of higher-order components such as the second- or higher-order components is extended compared to local Bo shimming current of the first-order components (x, y, and z components). In the practical example 4, only the first-order components of local Bo shimming current are changed in the selected region 1 and selected region 2, and higher-order components are shared in the selected region 1 and selected region 2. Consequently, although an overview of a process flow for setting local Bo shimming current and a post-adjustment excitation frequency is the same as the practical example 3 described before, the details of a calculation algorithm of a post-adjustment excitation frequency for the selected region 2 vary. Hereinafter, with focus mainly on differences from the practical example 3, the practical example 4 will be described in detail.

(Calculation for a Post-Adjustment Excitation Frequency)

First, an overview of a calculation method for a post-adjustment excitation frequency according to static magnetic field inhomogeneity distribution in the respective regions of the present practical example 4 will be described.

After measuring static magnetic field inhomogeneity distribution, local Bo shimming current ($C_1$) and a post-adjustment excitation frequency ($f0_1'$) for the selected region 1 are calculated. The calculation method is similar to the practical example 3 described before.

Next, local Bo shimming current $(C)_2=[Gx_2, Gy_2, Gz_2, Gxy_2]$ for the selected region 2 is calculated. Then, a post-adjustment excitation frequency ($f0_2'$) for the selected region 2 is calculated. On a static magnetic field inhomogeneity estimation map after shimming for the calculation, the first-order components $[Gx_2, Gy_2, Gz_2]$ of local Bo shimming current for the selected region 2 and the higher-order components $[Gxy_1]$ such as the second- or higher-order of local Bo shimming current ($C_1$) for the selected region 1 are used. That is, when calculating a frequency offset $\Delta f0_2$ in the selected region 2 using the formula (2), $Gxy_2$ is converted into $Gxy_1$ so that a shim coil current value is C ($=[\Delta f0_2, Gx_2, Gy_2, Gz_2, Gxy_1]$). Additionally, when determining a post-adjustment excitation frequency $f0_2'$ in the selected region 2 using the formula (3), a frequency offset $<f0_2>$ is calculated based on a static magnetic field inhomogeneity estimation map after shimming in the selected region 2. Then, a static magnetic field inhomogeneity estimation map after shimming is estimated using the first-order components $[Gx_2, Gy_2, Gz_2]$ of local Bo shimming current for the selected region 2 and the higher-order components $[Gxy_1]$ such as the second- or higher-order of local Bo shimming current for the selected region 1.

The subsequent processes are similar to the practical example 3.

(Functional Block of the Practical Example 4)

Next, the respective functions of the processing unit 114 to achieve a region imaging method of the present practical example 4 will be described. The functional block of the processing unit 114 related to the present practical example 4 is similar to that of the practical example 3 described before, but the functions of the excitation frequency calculation unit 304 vary. Hereinafter, only differences from the above practical example 3 will be described, and descriptions of the same contents will be omitted.

The excitation frequency calculation unit 304 sets a post-adjustment excitation frequency to excite a selected region so that static magnetic field inhomogeneity in a selected region is reduced similarly to the practical example 3 described before. However, when calculating a frequency offset $\Delta f0_2$ in the selected region 2, the higher-order components $[Gxy_1]$ such as the second- or higher-order of local Bo shimming current $(C)_1=[Gx_1, Gy_1, Gz_1, Gxy_1]$ for the selected region 1 is used. That is, C ($=[\Delta f0_2, Gx_2, Gy_2, Gz_2, Gxy_1]$) is used as the formula (2). Also, a static magnetic field inhomogeneity estimation map after shimming in the selected region 2 when a frequency offset $<f0_2>$ is calculated using the formula (3) is estimated using the first-order components $[Gx_1, Gy_1, Gzv]$ of local Bo shimming current for the selected region 2 and the higher-order components $[Gxy_1]$ such as the second- or higher-order of local Bo shimming current for the selected region 1.

(Process Flow of the Practical Example 4)

Next, the process flow of the present practical example 4 for which the above respective functional units cooperate with each other will be described. The process flow of the present practical example 4 is similar to the process flow in FIG. 8 described in the practical example 3 described before, but the process contents in Steps 805, 807, and 810 vary. Hereinafter, only different steps from the above practical example 3 will be described, and step descriptions of the same process contents will be omitted.

In Step 805, the excitation frequency calculation unit 304 sets a post-adjustment excitation frequency ($f0_2'$) in the selected region 2 so that static magnetic field inhomogeneity in the selected region 2 is reduced. In this case, the higher-order components $[Gxy_1]$ such as the second- or higher-order of local Bo shimming current for the selected region 1 is used instead of the higher-order components $[Gxy_2]$ such as the second- or higher-order of local Bo shimming current for the selected region 2. The details are as described before.

In Step 805, the setting unit 306 sets higher-order components such as the first- and second- or higher-order of local Bo shimming current ($C_1$) calculated in Step 802 and a post-adjustment excitation frequency ($f0_1'$) calculated in Step 803 respectively as local Bo shimming current and a post-adjustment excitation frequency for when exciting the selected region 1, generates control data in an imaging sequence to be described later, and then notifies the control data to the measurement control unit 111. Similarly, the setting unit 306 sets only the first-order components of local Bo shimming current ($C_2$) calculated in Step 804 and a post-adjustment excitation frequency ($f0_2'$) calculated in Step 805 respectively as local Bo shimming current and a post-adjustment excitation frequency for when exciting the selected region 2, generates control data in an imaging sequence to be described later, and then notifies the control data to the measurement control unit 111.

In Step 810, the measurement control unit 111 controls imaging for the selected region 1 and selected region 2 using local Bo shimming current ($C_1$, $C_2$) and a post-adjustment excitation frequency ($f0_1'$, $f0_2'$) of the selected region 1 and selected region 2 set in Step 807.

Figure 10:
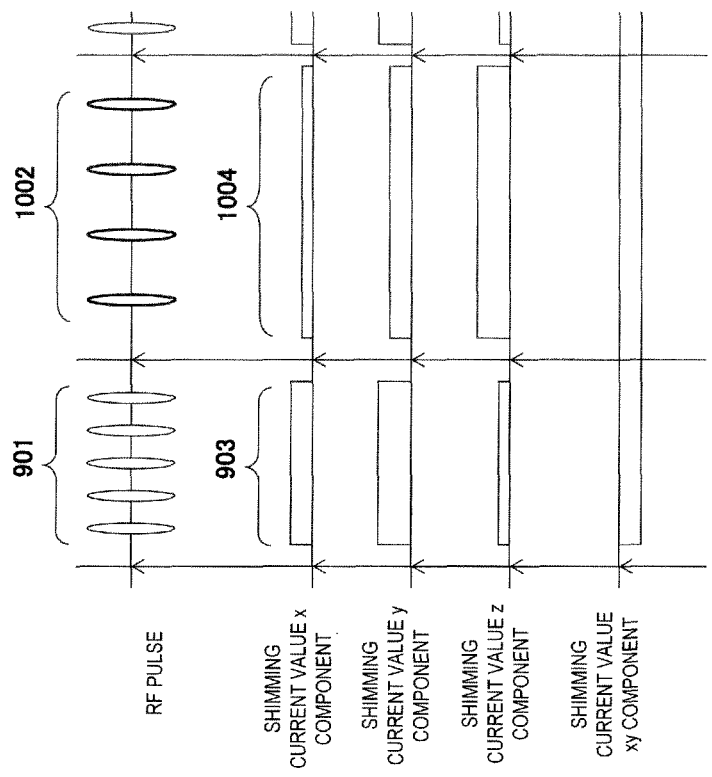
FIG. 10 is a sequence chart of the practical example 4.

For example, excitation for the selected region 1 is started after setting higher-order components such as the first- and second- or higher-order of a post-adjustment excitation frequency ($f0_1'$) and local Bo shimming current ($C_1$) in the selected region 1 when an imaging sequence shown in a sequence chart in FIG. 10 is used. Similarly to FIG. 9, while set local Bo shimming current ($C_1$) is being applied to each shim coil (903), the RF pulse (901) is irradiated.

When excitation for the selected region 1 is completed, only the first-order components of a post-adjustment excitation frequency ($f0_2'$) and local Bo shimming current ($C_2$) in the selected region 2 are set, a same value as the selected region 1 is used for higher-order components such as the second- or higher-order of local Bo shimming current, and then excitation for the selected region 2 is started. Then, while set local Bo shimming current ($C_2$) is being applied to each shim coil (1004), the RF pulse (1002) is irradiated.

These are the descriptions of the process flow of the present practical example 4.

As described above, in an MRI apparatus and a region imaging method of the present practical example 4, the second- or higher-order components of local Bo shimming current are the same values among the respective selected regions. Consequently, waiting for a response delay of the second- or higher-components of local Bo shimming current for when excitation shifts from the selected region 1 to the selected region 2 is not needed, resulting in that excitation can shift from the selected region 1 to the selected region 2 instantly. Therefore, when imaging multiple selected regions, reducing restrictions of imaging conditions and imaging time can be performed.

Practical Example 5

Next, the practical example 5 for an MRI apparatus and a region imaging method of the present invention will be described. The practical example 5 uses local Bo shimming current common to each region. Therefore, the practical example 5 is suitable for when the selected region 2 in FIG. 2(*c*) is included in the selected region 1. Hereinafter, the present practical example 5 will be described in detail.

(Functional Block of the Practical Example 5)

First, the respective functions of the processing unit 114 to achieve a region imaging method of the present practical example 5 will be described. The functional block of the processing unit 114 related to the present practical example 5 is similar to that of the practical example 3 described before, but the functions of the excitation frequency calculation unit 304 vary. Hereinafter, only differences from the above practical example 3 will be described, and descriptions of the same contents will be omitted.

The excitation frequency calculation unit 304 sets a post-adjustment excitation frequency to excite a selected region so that static magnetic field inhomogeneity in a selected region is reduced similarly to the practical example 3 described before. However, when calculating a frequency offset $\Delta f0_2$ in the selected region 2, local Bo shimming current $(C)_1 = [Gx_1, Gy_1, Gz_1, Gxy_1]$ for the selected region 1 is used. That is, $C_2 \ (= [\Delta f0_2, Gx_1, Gy_1, Gz_1, Gxy_1])$ is used as the formula (2). Also, a static magnetic field inhomogeneity estimation map after shimming in the selected region 2 when a frequency offset $<f0_2>$ is calculated using the formula (3) is estimated using local Bo shimming current $[Gx_1, Gy_1, Gz_1, Gxy_1]$ for the selected region 1.

(Process Flow of the Practical Example 5)

Next, the process flow of the present practical example 5 for which the above respective functional units cooperate with each other will be described. Compared to the practical example 3 described before, the process flow of the present practical example 5 does not have the Step 804 process, and the process contents in Steps 805 and 810 vary. Hereinafter, only different steps from the above practical example 3 will be described, and step descriptions of the same process contents will be omitted.

In Step 805, the excitation frequency calculation unit 304 sets a post-adjustment excitation frequency ($f0_2'$) in the selected region 2 so that static magnetic field inhomogeneity in the selected region 2 is reduced. In this case, local Bo shimming current $(C)_1 = [Gx_1, Gy_1, Gz_1, Gxy_1]$ for the selected region 1 is used as local Bo shimming current for the selected region 2. The details are as described before.

In Step 810, the measurement control unit 111 controls imaging for the selected region 1 and selected region 2 using local Bo shimming current ($C_1$, $C_2=C_1$) and a post-adjustment excitation frequency ($f0_1'$, $f0_2'$) of the selected region 1 and selected region 2 set in Step 807.

Figure 11:
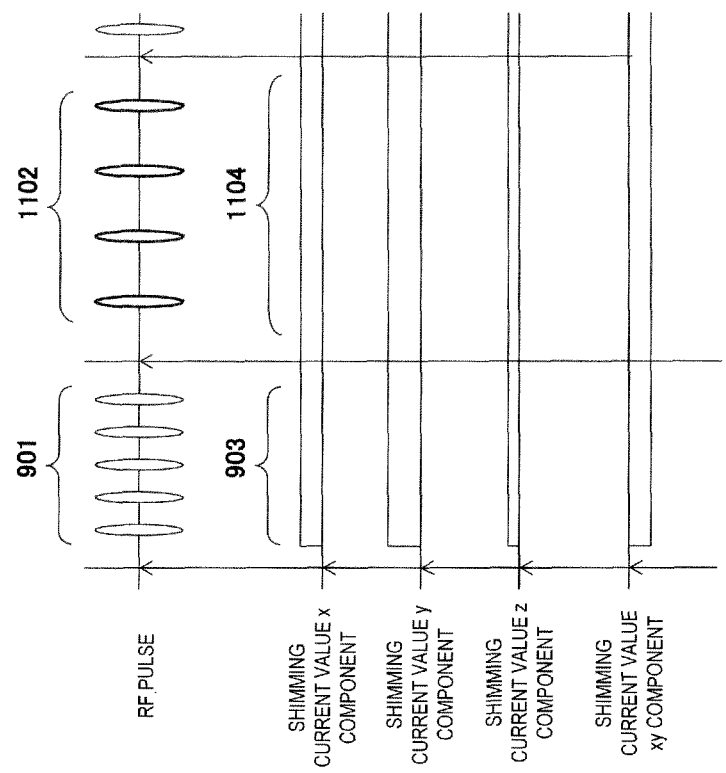
FIG. 11 is a sequence chart of the practical example 5.

For example, excitation for the selected region 1 is started after setting a post-adjustment excitation frequency ($f0_1'$) and local Bo shimming current ($C_1$) in the selected region 1 when an imaging sequence shown in a sequence chart in FIG. 11 is used. Similarly to FIG. 9, while set local Bo shimming current ($C_1$) is being applied to each shim coil (903), the RF pulse (901) is irradiated.

When excitation for the selected region 1 is completed, only a post-adjustment excitation frequency ($f0_2'$) in the selected region 2 are set, local Bo shimming current ($C_1$) in the selected region 1 is used as local Bo shimming current ($C_2$) in the selected region 2 as it is, and then excitation for the selected region 2 is started. Then, similarly to FIG. 9, while set local Bo shimming current ($C_1$) is being applied to each shim coil (1104), the RF pulse (1102) is irradiated.

These are the descriptions of the process flow of the present practical example 5.

As described above, in an MRI apparatus and a region imaging method of the present practical example 5, all the components of local Bo shimming current for each selected region are the same values respectively. Consequently, when exciting multiple selected regions sequentially, changing a value of local Bo shimming current is not needed, resulting in that multiple selected regions can be sequentially imaged in an easy and high-speed manner.

Practical Example 6

Next, the practical example 6 for an MRI apparatus and a region imaging method of the present invention will be described. The present practical example 6 is an example that executes any of the respective practical examples 3 to 5 described before in order to secure the minimum static magnetic field homogeneity.

As described before, in the light of static magnetic field inhomogeneity, homogeneity is the lowest in the method of the practical example 5, the next-lowest in the method of the practical example 4, and the highest in the method of the practical example 3. Therefore, the present practical example 6 judges the respective practical examples in this order to adopt a method of a practical example that fulfills predetermined determination criteria, and then sets local Bo shimming current and a post-adjustment excitation frequency for each selected region. Hereinafter, the present practical example 6 will be described in detail.

(Process Flow of the Practical Example 6)

The process flow of the present practical example 6 will be described based on a flow chart shown in FIG. 12. The present process flow is memorized as a program in the internal memory unit 115 in advance and is performed by the processing unit 114 reading the program from the internal memory unit 115. Hereinafter, the process contents of the respective process steps will be described in detail.

In Step 1200, similarly to the practical example 3 described before, the selected region 1 and selected region 2 are set on a layout image.

In Step 1201, similarly to the practical example 3 described before, static magnetic field inhomogeneity distribution of a region including the selected region 1 and selected region 2 is measured.

In Step 1202, according to the practical example 3 described before, local Bo shimming current ($C_1$) and a post-adjustment excitation frequency ($f0_1'$) for the selected region 1 are calculated. The details are as the practical example 3 described before.

In Step 1203, according to the practical example 3 described before, local Bo shimming current ($C_2$) and a post-adjustment excitation frequency ($f0_2'$) for the selected region 2 are calculated.

In Step 1204, the determination unit 705 determines whether static magnetic field inhomogeneity (i.e., a static magnetic field inhomogeneity estimation map after shimming) for the selected region 1 and selected region 2 for when local Bo shimming current and a post-adjustment excitation frequency set in Steps 1202 and 1203 are used fulfills predetermined determination criteria or not. The determination criteria are, for example, that the distribution is a threshold value (100 Hz) or less, that a difference between the maximum value and the minimum value is a threshold value or less, etc. for static magnetic field inhomogeneity distribution in a region on a static magnetic field inhomogeneity estimation map after shimming. If the determination conditions are fulfilled (Yes), the procedure proceeds to Step 1209. If the determination conditions are not fulfilled (No), the procedure proceeds to Step 1205.

In Step 1205, according to the practical example 4 described before, local Bo shimming current ($C_2$) and a post-adjustment excitation frequency ($f0_2'$) for the selected region 2 are calculated again. The details are as the practical example 4 described before.

In Step 1206, the determination unit 705 determines whether static magnetic field inhomogeneity (i.e., a static magnetic field inhomogeneity estimation map after shimming) for the selected region 2 for when local Bo shimming current ($C_2$) and a post-adjustment excitation frequency ($f0_2'$) set in Step 1205 are used fulfills predetermined determination criteria or not. The determination criteria are the same as those in Step 1204. If the determination criteria are fulfilled (Yes), the procedure proceeds to Step 1209. If the determination criteria are not fulfilled (No), the procedure proceeds to Step 1207.

In Step 1207, according to the practical example 3 described before, local Bo shimming current ($C_2$) and a post-adjustment excitation frequency ($f0_2'$) for the selected region 2 are calculated again.

In Step 1208, the determination unit 705 determines whether static magnetic field inhomogeneity (i.e., a static magnetic field inhomogeneity estimation map after shimming) for the selected region 2 for when local Bo shimming current ($C_2$) and a post-adjustment excitation frequency ($f0_2'$) set in Step 1207 are used fulfills predetermined determination criteria or not. The determination criteria are the same as those in Step 1204. If the determination criteria are fulfilled (Yes), the procedure proceeds to Step 1209. If the determination criteria are not fulfilled (No), the procedure proceeds to Step 1210.

In Step 1209, the setting unit 306 sets a value calculated in Step 1202 for an imaging parameter that sets local Bo shimming current ($C_1$) and a post-adjustment excitation frequency ($f0_1'$) for when exciting the selected region 1. Similarly, the setting unit 306 sets a value calculated in any method of the practical examples 3 to 5 that fulfill determination conditions for an imaging parameter that sets local Bo shimming current ($C_2$) and a post-adjustment excitation frequency ($f0_2'$) for when exciting the selected region 2.

In Step 1210, the measurement control unit 111 controls imaging for the selected region 1 and selected region 2 using local Bo shimming current ($C_1$, $C_2$) and a post-adjustment excitation frequency ($f0_1'$, $f0_2'$) of the selected region 1 and selected region 2 set in Step 1209. The change processes of a post-adjustment excitation frequency and local Bo shimming current are to follow the practical examples 3, 4, and 5.

In Step 1211, the determination unit 705 displays a warning and beeps on the display and operation unit 118 when imaging conditions have to be changed due to that determination conditions are not fulfilled.

In Step 1212, settings such as an imaging parameter are performed again so that static magnetic field inhomogeneity distribution in the selected region 1 and selected region 2 fulfills predetermined determination criteria. For example, re-adjustment of the selected region 1 and selected region 2, TR extension in case of an SSFP sequence, and re-adjustment of excitation positions in case of a pencil beam are performed. Then, the procedure proceeds to Step 1201 to measure static magnetic field inhomogeneity distribution again, and processes in the above respective steps are repeated.

These are the descriptions of the process flow of the present practical example 6.

As described above, in an MRI apparatus and a region imaging method of the present practical example 6, shimming current is calculated respectively for a single selected region using a plurality of methods, among the methods that fulfill predetermined determination criteria, and the shimming current of which the change amount is the least compared to other selected regions is set for the single selected region. Consequently, because the simplest shimming current can be calculated according to static magnetic field inhomogeneity distribution is a selected region to be excited, imaging for each selected region can be optimized according to the static magnetic field inhomogeneity distribution in the selected region.

Additionally, in the practical examples 3 to 6 described before, examples where frequency control for each selected region, that is, a post-adjustment excitation frequency ($f0'$) of an RF pulse according to the static magnetic field inhomogeneity for each selected region is calculated and applied were described. However, if a main sequence that excites a selected region is an SSFP sequence, an increment (RF-Phase) may be calculated from a post-adjustment excitation frequency ($f0'$) or a phase rotation amount equivalent to a frequency amount (Δf0+<f0>) corresponding to static magnetic field inhomogeneity to apply phase control to the RF pulse in the selected region.

Practical Example 7

Next, the practical example 7 for an MRI apparatus and a region imaging method of the present invention will be described. The present practical example 7, taking a single region as a selected region, applies frequency control for a pre-pulse sequence and phase control for a main (SSFP) sequence when using the pre-pulse sequence that precedes the main sequence concurrently with an SSFP sequence as a main sequence. Therefore, the present practical example 7 is basically similar to the practical example 1 or practical example 2 described before, but varies in that an excitation frequency (f0') calculated so that static magnetic field inhomogeneity of a selected region is reduced is an excitation frequency of a pre-pulse sequence. Hereinafter, differences from the practical example 1 or practical example 2 described before will be mainly described, and descriptions of the same contents will be omitted.

(Functional Block of the Practical Example 7)

Because the respective functions of the processing unit 114 to achieve a region imaging method of the present practical example 7 are similar to the functional block of the practical example 1 or practical example 2 described before, the descriptions will be omitted.

(Process Flow of the Practical Example 6)

Figure 4:
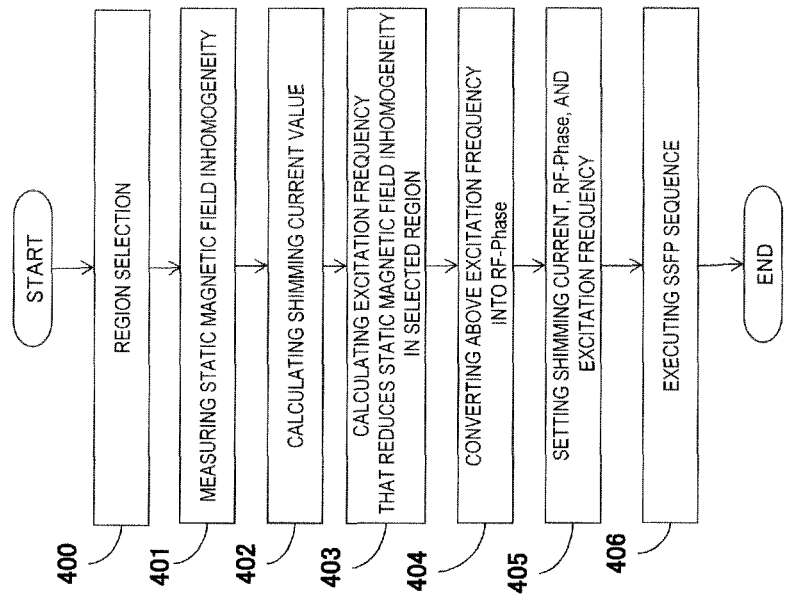
FIG. 4 is a flow chart showing a process flow of the practical example 1.

Although the process flow of the present practical example 7 is basically similar to that shown in FIG. 4 described in the practical example 1 or practical example 2 described before, the process contents in Steps 405 and 406 vary. Hereinafter, only differences from the practical example 1 or practical example 2 described before will be described, and descriptions of the same contents will be omitted.

In Step 405, in addition to the process contents in Step 404 of the practical example 1, the setting unit 306 takes an excitation frequency (f0') calculated in Step 403 as an excitation frequency of a pre-pulse sequence. Then, control data of a pre-pulse sequence and main sequence is generated and notified to the measurement control unit 111.

In Step 406, the measurement control unit 111 controls the pre-pulse sequence execution using local Bo shimming current (C) and a post-adjustment excitation frequency (f0') set in Step 405 and controls the main sequence execution using the same local Bo shimming current (C) and RF-Phase as well as a post-adjustment excitation frequency (f0).

These are the descriptions of the process flow of the present practical example 7.

As described above, when exciting a selected region using an imaging sequence that is comprised of a pre-pulse sequence and SSFP sequence, an MRI apparatus and a region imaging method of the practical example 7 calculates shimming current and a post-adjustment excitation frequency (f0') according to static magnetic field inhomogeneity distribution of the selected region and calculates RF-Phase corresponding to a post-adjustment excitation frequency (f0'). Then, shimming current and a post-adjustment excitation frequency (f0') are applied to a pre-pulse sequence, and the same shimming current and increment (RF-Phase) are applied to an SSFP sequence. Consequently, image quality deterioration due to static magnetic field inhomogeneity distribution of a selected region can be reduced. Also, because the position of band artifacts is controlled by RF-Phase similarly to the practical example 1 described before, the position of band artifacts can be fixed at the same position without changing the position even after an operator changes a post-adjustment excitation frequency (f0).

Practical Example 8

Next, the practical example 8 for an MRI apparatus and a region imaging method of the present invention will be described. The present practical example 8 takes an SSFP sequence as a main sequence in case of taking multiple regions as a selected region, and then excites the selected region 1 using frequency control in a pre-pulse sequence and excites the selected region 2 using phase control in an SSFP sequence in case of concurrently using a pre-pulse sequence that precedes this main sequence.

a single region as a selected region, applies frequency control for a pre-pulse sequence and phase control for a main (SSFP) sequence when using the pre-pulse sequence that precedes the main sequence concurrently with an SSFP sequence as a main sequence. Therefore, the present practical example 8 is basically similar to the practical examples 3 to 6 described before for a pre-pulse sequence and is similar to the practical example 1 or 2 described before for an SSFP sequence. However, control of shimming current in both selected regions is similar to the practical examples 3 to 6 described before. Hereinafter, differences from the respective practical examples described before will be described, and descriptions of the same contents will be omitted.

(Functional Block of the Practical Example 8)

The respective functions of the processing unit 114 to achieve a region imaging method of the present practical example 8 will be described based on FIGS. 13(a) and 13(b). Although the respective functions of the present practical example are basically similar to the functional block described using FIGS. 3(a) and 3(b) in the practical example 1 or 2 described before, a calculated post-adjustment excitation frequency (f0') is notified from the excitation frequency calculation unit 304 to the setting unit 306 in order to excite the selected region 1 in a pre-pulse sequence of frequency control.

Figure 7:
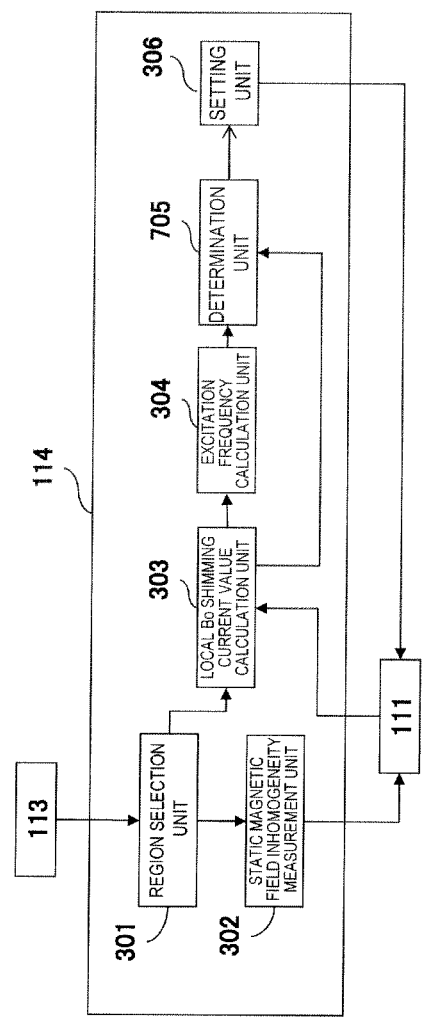
FIG. 7 is a functional block diagram of the practical example 3.

Then, the configuration and operation for when local Bo shimming current (C) and a post-adjustment excitation frequency (f0') are calculated by a pre-pulse sequence to excite the selected region 1 are similar to those of the functional block shown in FIG. 7 in the practical example 3 described before. Also, the configuration and operation for when local Bo shimming current (C), RF-Phase, and a post-adjustment excitation frequency (f0) are calculated by a main (SSFP) sequence to excite the selected region 2 are similar to those of the functional block shown in FIGS. 3(a) and 3(b) in the practical example 1 or 2 described before.

(Process Flow of the Practical Example 8)

Next, the process flow of the present practical example 8 for which the above respective functional units cooperate with each other will be described. The process flow of the present practical example 8 is basically similar to the process flow in FIG. 8 described in the practical example 3 described before, but the process contents in Steps 807 and 810 vary. Hereinafter, only differences from the practical example 3 described before will be described, and descriptions of the same contents will be omitted.

In Step 807, the RF-Phase calculation unit 305 calculates RF-Phase corresponding to a post-adjustment excitation frequency (f0$_2$') calculated in Step 805 as RF-Phase for when the selected region 2 is excited.

Then, the setting unit 306 sets local Bo shimming current ($C_1$) calculated in Step 802 and a post-adjustment excitation frequency ($f0_1'$) calculated in Step 803 respectively as local Bo shimming current and a post-adjustment excitation frequency for when the selected region 1 is excited, generates control data of a pre-pulse sequence to be described later, and then notifies to the measurement control unit 111. Similarly, the setting unit 306 sets local Bo shimming current ($C_2$) calculated in Step 804 and RF-Phase calculated in the RF-Phase calculation unit 305 above respectively as local Bo shimming current and RF-Phase for when the selected region 2 is excited, generates control data of a main (SSFP) sequence to be described later, and then notifies to the measurement control unit 111.

In Step 810, the measurement control unit 111 controls excitation for the selected region 1 by a pre-pulse sequence using local Bo shimming current ($C_1$) and a post-adjustment excitation frequency ($f0_1'$) set in Step 807. Then, the measurement control unit 111 controls excitation for the selected region 2 by a main (SSFP) sequence using local Bo shimming current ($C_1$), RF-Phase, and a post-adjustment excitation frequency ($f0$) set in Step 807.

These are the descriptions of the process flow of the present practical example 8.

As described above, an MRI apparatus and a region imaging method of the present practical example 8 calculates local Bo shimming current and a post-adjustment excitation frequency or an increment (RF-Phase) according to the static magnetic field inhomogeneity distribution for each selected region, changes local Bo shimming current and a post-adjustment excitation frequency or RF-Phase for each selected region, and then excites the respective selected regions. Consequently, when a plurality of selected regions are excited separately, local Bo shimming current and a post-adjustment excitation frequency or RF-Phase optimum according to static magnetic field inhomogeneity distribution for each selected region are used, which can reduce image quality deterioration due to static magnetic field inhomogeneity distribution for each selected region.

REFERENCE SIGNS LIST

101: object, 102: static magnetic field generation magnet, 103: gradient magnetic field coil, 104: RF transmission coil, 105: RF receiving coil, 106: bed, 107: signal process unit, 108: total control unit, 109: gradient magnetic field power source, 110: RF transmission unit, 111: measurement control unit, 118: display and operation unit, 114: processing unit (CPU), 115: internal memory unit, 116: network IF, 117: external memory unit

The invention claimed is:

1. A region imaging method for a magnetic resonance imaging apparatus that includes a shimming unit where static magnetic field inhomogeneity is reduced after shimming current is supplied, the region imaging method comprising:
   measuring the static magnetic field inhomogeneity;
   calculating shimming current based on the static magnetic field inhomogeneity;
   calculating an increment (RF-Phase) in an irradiation phase of an RF pulse to be used in a pulse sequence based on the static magnetic field inhomogeneity; and
   measuring an echo signal from an object by changing an irradiation phase of the RF pulse for each increment in a state where the static magnetic field inhomogeneity is reduced after the shimming current is supplied to the shimming unit.

2. A magnetic resonance imaging apparatus comprising:
   a static magnetic field generation unit that generates a static magnetic field in an imaging region where an object is placed;
   a shimming unit that generates a compensation magnetic field that reduces static magnetic field inhomogeneity where the static magnetic field is spatially inhomogeneous after shimming current is supplied;
   a measurement control unit that controls measurement of an echo signal from the object based on a predetermined pulse sequence;
   a static magnetic field inhomogeneity measurement unit that calculates the static magnetic field inhomogeneity using the echo signal;
   a shimming current calculation unit that calculates the shimming current based on the static magnetic field inhomogeneity;
   an RF-Phase calculation unit that calculates an increment (RF-Phase) of an irradiation phase of an RF pulse to be used in a pulse sequence based on the static magnetic field inhomogeneity; and
   a measurement control unit that controls measurement of an echo signal from the object by applying phase control that changes an irradiation phase of the RF pulse for each increment in a state where the static magnetic field inhomogeneity is reduced after the shimming current is supplied to the shimming unit.

3. The magnetic resonance imaging apparatus according to claim 2, comprising:
   a region selection unit that accepts settings for a selected region that reduces the static magnetic field inhomogeneity,
   wherein the shimming current calculation unit calculates the shimming current based on static magnetic field inhomogeneity of the selected region, and
   the RF-Phase calculation unit calculates the increment (RF-Phase) based on static magnetic field inhomogeneity of the selected region.

4. The magnetic resonance imaging apparatus according to claim 3,
   wherein the region selection unit accepts settings for a plurality of selected regions,
   the shimming current calculation unit calculates shimming current for each selected region based on static magnetic field inhomogeneity for each selected region,
   the magnetic resonance imaging apparatus further comprises an excitation frequency calculation unit that calculates a post-adjustment excitation frequency of the RF pulse in a state where the static magnetic field inhomogeneity is reduced for each selected region, and
   the RF-Phase calculation unit calculates the increment (RF-Phase) for each selected region based on a post-adjustment excitation frequency for each selected region.

5. The magnetic resonance imaging apparatus according to claim 2, comprising:
   an excitation frequency calculation unit that calculates a post-adjustment excitation frequency which is an excitation frequency of the RF pulse in a state where the static magnetic field inhomogeneity is reduced after a frequency amount corresponding to the static magnetic field inhomogeneity is added to an excitation frequency of the RF pulse used when the static magnetic field inhomogeneity measurement unit calculates the static magnetic field inhomogeneity, wherein the RF-Phase calculation unit calculates the increment (RF-Phase) based on the post-adjustment excitation frequency.

6. The magnetic resonance imaging apparatus according to claim 5,
wherein the excitation frequency calculation unit calculates a post-adjustment excitation frequency based on a state where the static magnetic field inhomogeneity is reduced.

7. The magnetic resonance imaging apparatus according to claim 5,
wherein the pulse sequence is comprised of a pre-pulse sequence and SSFP sequence, and
the measurement control unit applies frequency control that takes the excitation frequency as the post-adjustment excitation frequency for an RF pulse of the pre-pulse sequence and applies the phase control to the irradiation phase for an RF pulse of the SSFP sequence.

8. The magnetic resonance imaging apparatus according to claim 7,
wherein, if the pre-pulse sequence and the SSFP sequence excite different selected regions,
the shimming current calculation unit calculates shimming current for each selected region based on static magnetic field inhomogeneity for each selected region,
the excitation frequency calculation unit calculates a post-adjustment excitation frequency of the RF pulse in a state where the static magnetic field inhomogeneity is reduced for each selected region, and
the RF-Phase calculation unit calculates the increment (RF-Phase) in a selected region excited by the SSFP sequence based on a post-adjustment excitation frequency in the selected region.

9. The magnetic resonance imaging apparatus according to claim 2,
wherein the RF-Phase calculation unit calculates the increment (RF-Phase) as a phase rotation amount equivalent to a frequency amount corresponding to the static magnetic field inhomogeneity.

10. The magnetic resonance imaging apparatus according to claim 9, comprising:
an adjustment value input unit where an adjustment value ($\phi$) of the increment (RF-Phase) is input,
wherein the RF-Phase calculation unit calculates the increment (RF-Phase) using the adjustment value ($\phi$).

11. The magnetic resonance imaging apparatus according to claim 2, wherein the pulse sequence is an SSFP sequence, and the measurement control unit applies the phase control to an irradiation phase of an RF pulse in the SSFP sequence.

12. A magnetic resonance imaging apparatus comprising:
a static magnetic field generation unit that generates a static magnetic field in an imaging region where an object is placed;
a shimming unit that generates a compensation magnetic field that reduces static magnetic field inhomogeneity where the static magnetic field is spatially inhomogeneous after shimming current is supplied;
a measurement control unit that controls measurement of an echo signal from the object based on a predetermined pulse sequence;
a static magnetic field inhomogeneity measurement unit that calculates the static magnetic field inhomogeneity using the echo signal;
a processing unit that calculates the shimming current based on the static magnetic field inhomogeneity and calculates a post-adjustment excitation frequency of an RF pulse of the pulse sequence in a state where the static magnetic field inhomogeneity is reduced after the shimming current is supplied to the shimming unit; and
a region selection unit accepts settings for a plurality of selected regions,
wherein the processing unit calculates the shimming current and the post-adjustment excitation frequency for each selected region according to how a plurality of selected regions overlap, and
the measurement control unit controls measurement of the echo signal using the post-adjustment excitation frequency for an RF pulse of the pulse sequence in a state where the static magnetic field inhomogeneity is reduced after the shimming current is supplied to the shimming unit.

13. The magnetic resonance imaging apparatus according to claim 12, wherein, if two regions do not overlap partially with each other at least,
the processing unit calculates the shimming current and the post-adjustment excitation frequency according to the static magnetic field inhomogeneity distribution for each selected region, and
the measurement control unit controls measurement of an echo signal from each selected region by changing the shimming current and the post-adjustment excitation frequency for each selected region.

14. The magnetic resonance imaging apparatus according to claim 12,
wherein the processing unit takes the second- or higher-components of the shimming current for each selected region as the same values.

15. The magnetic resonance imaging apparatus according to claim 12,
wherein, if one region includes another region,
the processing unit takes all the components of the shimming current for each selected region as the same values respectively.

* * * * *